United States Patent
Thompson et al.

(10) Patent No.: US 10,456,208 B2
(45) Date of Patent: Oct. 29, 2019

(54) SURGICAL CANNULA MOUNTS AND RELATED SYSTEMS AND METHODS

(71) Applicant: Intuitive Surgical Operations, Inc., Sunnyvale, CA (US)

(72) Inventors: Allen C. Thompson, Los Altos, CA (US); Randal P. Goldberg, San Mateo, CA (US); Dean F. Hoornaert, San Jose, CA (US); Tyler J. Morrissette, Niantic, CT (US); Bruce M. Schena, Menlo Park, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 322 days.

(21) Appl. No.: 15/126,725

(22) PCT Filed: Mar. 17, 2015

(86) PCT No.: PCT/US2015/020916
§ 371 (c)(1),
(2) Date: Sep. 16, 2016

(87) PCT Pub. No.: WO2015/142814
PCT Pub. Date: Sep. 24, 2015

(65) Prior Publication Data
US 2017/0086930 A1    Mar. 30, 2017

Related U.S. Application Data
(60) Provisional application No. 61/954,222, filed on Mar. 17, 2014.

(51) Int. Cl.
*A61B 34/35*    (2016.01)
*A61B 34/30*    (2016.01)
(Continued)

(52) U.S. Cl.
CPC .......... *A61B 34/35* (2016.02); *A61B 17/3476* (2013.01); *A61B 34/30* (2016.02);
(Continued)

(58) Field of Classification Search
CPC ......... A61B 34/35; A61B 34/32; A61B 34/30; A61B 34/00; A61B 34/70; A61B 17/3476;
(Continued)

(56) References Cited

U.S. PATENT DOCUMENTS 5,553,198 A * 9/1996 Wang ..................... A61B 34/70
606/19
5,571,091 A    11/1996 Davis et al.
(Continued)

FOREIGN PATENT DOCUMENTS

CN    101627921 A    1/2010
CN    102119872 A    7/2011
(Continued)

OTHER PUBLICATIONS

International Search Report and Written Opinion for Application No. PCT/US15/20916, dated Jun. 19, 2015, 11 pages.
(Continued)

*Primary Examiner* — Terrell L McKinnon
*Assistant Examiner* — Michael McDuffie
(74) *Attorney, Agent, or Firm* — Jones Robb, PLLC

(57) ABSTRACT

A cannula mount for a surgical system may include a body having an aperture to receive a portion of a cannula. The cannula mount may further include a pivotable clamping arm to engage the portion of the cannula received in the aperture. The clamping arm may include a cam follower surface. The cannula mount may further include a block moveable between a first position and a second position. The block may include a cam surface. The cam surface of the
(Continued)

block may engage the cam follower surface of the clamping arm in the first position to actuate the clamping arm to a closed position in which the clamping arm engages the portion of the cannula received in the aperture. The clamping arm may be permitted to move to an open position in which the clamping arm does not engage the cannula when the block is in the second position.

23 Claims, 25 Drawing Sheets

(51) Int. Cl.
*A61B 46/10* (2016.01)
*A61B 17/34* (2006.01)
*A61B 17/00* (2006.01)
*A61B 90/00* (2016.01)

(52) U.S. Cl.
CPC .............. *A61B 46/10* (2016.02); *A61B 17/34* (2013.01); *A61B 2017/00477* (2013.01); *A61B 2017/00862* (2013.01); *A61B 2017/00876* (2013.01); *A61B 2090/0808* (2016.02)

(58) Field of Classification Search
CPC ............ A61B 46/10; A61B 2090/0808; A61B 2017/00876; A61B 2017/00862; A61B 17/34; A61B 17/3421; A61B 2017/00477; A61B 2034/301–306
USPC ......... 248/685, 580, 222.13, 229.11, 229.13, 248/229.21, 229.23, 228.2, 230.2, 231.31, 248/314, 222.11, 220.22, 220.21, 223.41, 248/225.11
See application file for complete search history.

(56) References Cited

U.S. PATENT DOCUMENTS

| | | | |
|---|---|---|---|
| 6,758,454 B2 * | 7/2004 | Smed | F16M 11/10 248/278.1 |
| 7,666,191 B2 | 2/2010 | Orban, III | |
| 7,766,291 B2 * | 8/2010 | Eilmus | E03C 1/06 248/222.11 |
| 8,448,270 B2 * | 5/2013 | Yang | E03C 1/066 248/218.4 |
| 8,545,515 B2 | 10/2013 | Prisco et al. | |
| 8,888,059 B2 * | 11/2014 | Kohberg | B60K 15/067 248/201 |
| 9,532,849 B2 * | 1/2017 | Anderson | A61B 90/57 |
| 2006/0161136 A1 | 7/2006 | Anderson et al. | |
| 2011/0277775 A1 | 11/2011 | Holop et al. | |
| 2011/0277776 A1 * | 11/2011 | McGrogan | A61B 17/3423 128/852 |
| 2011/0282351 A1 | 11/2011 | Cooper et al. | |
| 2011/0290855 A1 * | 12/2011 | Moore | A61B 17/072 227/180.1 |
| 2012/0104071 A1 * | 5/2012 | Bryant | A61B 17/07207 227/175.1 |
| 2012/0245596 A1 | 9/2012 | Meenink | |
| 2012/0296281 A1 | 11/2012 | Jaspers et al. | |
| 2013/0325031 A1 | 12/2013 | Schena et al. | |
| 2013/0325033 A1 | 12/2013 | Schena et al. | |
| 2013/0338679 A1 | 12/2013 | Rosielle et al. | |
| 2015/0137760 A1 * | 5/2015 | Yang | F16M 11/041 320/115 |
| 2015/0282345 A1 * | 10/2015 | Aspinall | F16B 2/04 248/220.22 |
| 2018/0177557 A1 * | 6/2018 | Kapadia | A61B 34/30 |
| 2018/0317920 A1 * | 11/2018 | Guerrera | A61B 17/07207 |
| 2018/0318020 A1 * | 11/2018 | Thompson | A61B 34/30 |

FOREIGN PATENT DOCUMENTS

| | | |
|---|---|---|
| EP | 1931275 A1 | 6/2008 |
| WO | WO-02078767 A2 | 10/2002 |
| WO | WO-2007041094 A1 | 4/2007 |
| WO | WO-2011143021 A1 | 11/2011 |
| WO | WO-2011143024 A1 | 11/2011 |
| WO | WO-2012088471 A1 | 6/2012 |
| WO | WO-2013075205 A1 | 5/2013 |
| WO | WO-2015127231 A1 | 8/2015 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Extended European Search Report for Application No. 15764077.2, dated Aug. 2, 2017, 15 pages.

Office Action dated Aug. 7, 2018 for Chinese Application No. 2015800139549 filed Mar. 17, 2015, 18 pages.

* cited by examiner

SURGICAL CANNULA MOUNTS AND RELATED SYSTEMS AND METHODS

CROSS-REFERENCE TO RELATED APPLICATIONS

This application is a U.S. national stage application under 35 U.S.C. § 371(c) of International Application No. PCT/US2015/020916, filed on Mar. 17, 2015, which claims the benefit of priority to U.S. Provisional Application No. 61/954,222, filed on Mar. 17, 2014, each of which is hereby incorporated by reference in its entirety.

TECHNICAL FIELD

Aspects of the present disclosure relate to surgical cannulas, cannula mounts, and related systems and methods.

BACKGROUND

Remotely controlled surgical instruments, which can include teleoperated surgical instruments as well as manually operated (e.g., laparoscopic, thorascopic) surgical instruments, are often used in minimally invasive medical procedures. During surgical procedures, a surgical instrument that extends through a cannula inserted into a patient's body can be remotely manipulated to perform a procedure at a surgical site. For example, in a teleoperated surgical system, cannulas and surgical instruments can be mounted at manipulator arms of a patient side cart and be remotely manipulated via teleoperation at a surgeon console.

Generally, in teleoperated surgical procedures, a cannula is manually inserted in a patient at a desired incision site and, once positioned, is then docked to a mount on a manipulator arm. Cannula mounts have been useful and effective for surgical procedures, but still further improvements upon cannulas, cannula mounts, and the surgical systems that include them would be desirable.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, a cannula mount for a surgical system may comprise a body including an aperture to receive a portion of a cannula. The cannula mount may further comprise a pivotable clamping arm to engage the portion of the cannula received in the aperture. The clamping arm may comprise a cam follower surface. The cannula mount may further comprise a block moveable between a first position and a second position. The block may comprise a cam surface. The cam surface of the block may engage the cam follower surface of the clamping arm in the first position to actuate the clamping arm to a closed position in which the clamping arm engages the portion of the cannula received in the aperture. The clamping arm may be permitted to move to an open position in which the clamping arm does not engage the cannula when the block is in the second position.

In accordance with another exemplary embodiment, a cannula sterile adaptor for a surgical system may comprise a first portion and a second portion. The first portion may comprise a rigid material. The second portion may comprise a compliant material. The cannula sterile adaptor may comprise a depression to receive a clamping arm of a cannula mount of the surgical system. The first portion or the second portion may comprise the depression to receive the clamping arm.

In accordance with another exemplary embodiment, a cannula mount for a surgical system may comprise a body including an aperture to receive a portion of a cannula. The cannula mount may further comprise a plurality of pivotable clamping arms to engage the portion of the cannula received in the aperture. The cannula mount may further comprise a block moveable between a first position and a second position. The block may engage each of the clamping arms in the first position to actuate the plurality of clamping arms to a closed position in which the clamping arms engage the portion of the cannula received in the aperture.

In accordance with another exemplary embodiment, a teleoperated surgical system may comprise a cannula mount. The cannula mount may comprise a body including an aperture to receive a portion of a cannula. The cannula mount may further comprise a pivotable clamping arm to engage the portion of the cannula received in the aperture. The clamping arm may comprise a cam follower surface. The cannula mount may further comprise a block moveable between a first position and a second position. The block may comprise a cam surface. The cam surface of the block may engage the cam follower surface of the clamping arm in the first position to actuate the clamping arm to a closed position in which the clamping arm engages the portion of the cannula received in the aperture. The clamping arm may be permitted to move to an open position in which the clamping arm does not engage the cannula when the block is in the second position. The teleoperated surgical system may further comprise a cannula sterile adaptor and a cannula.

In accordance with another exemplary embodiment, a surgical cannula may comprise a bowl section, a tube, and an attachment portion. The attachment portion may extend from the bowl section, the attachment portion being configured to engage with at least one of a cannula sterile adaptor and a cannula mount of a surgical system. The attachment portion may extend from the bowl section along a radial direction with respect to a longitudinal axis of the cannula, the attachment portion tapering in a direction away from the bowl section.

In accordance with another exemplary embodiment, a cannula sterile adaptor for a surgical system comprises a sidewall forming a recess configured to receive an attachment portion of a cannula. At least one inner surface of the sidewall forms a recess having a shape corresponding to a shape of the attachment portion. The at least one inner surface of the sidewall comprises a protrusion in the at least one inner surface, the protrusion being configured to be inserted into a depression of the cannula attachment portion.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation.

DETAILED DESCRIPTION

Figure 1:
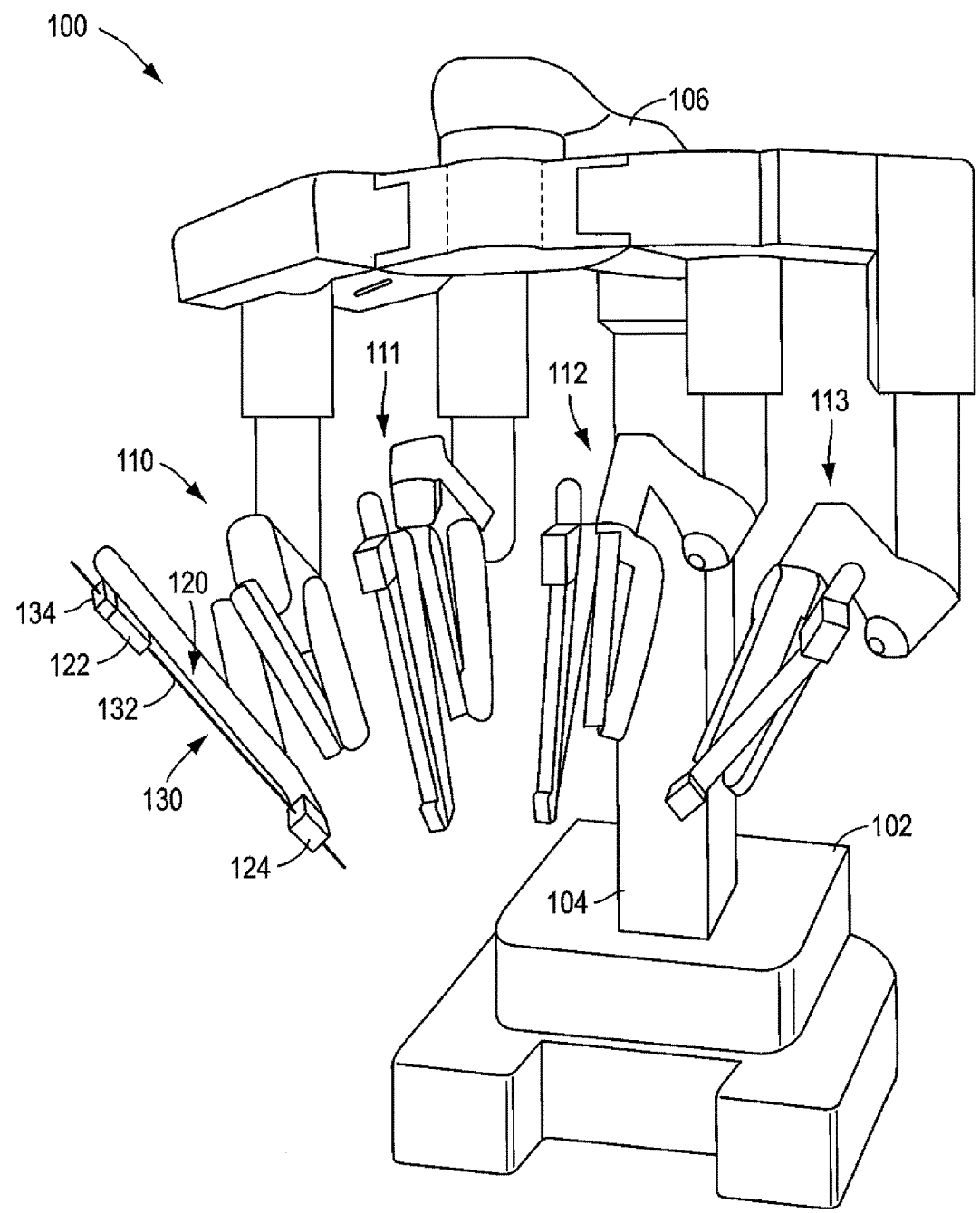
FIG. 1 is a perspective view of a patient side cart, according to an exemplary embodiment.

This description and the accompanying drawings that illustrate exemplary embodiments should not be taken as limiting. Various mechanical, compositional, structural, electrical, and operational changes may be made without departing from the scope of this description and the claims, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the disclosure or claims. For example, spatially relative terms—such as "beneath", "below", "lower", "above", "upper", "proximal", "distal", and the like—may be used to describe one element's or feature's relationship to another element or feature as illustrated in the orientation of the figures. These spatially relative terms are intended to encompass different positions (i.e., locations) and orientations (i.e., rotational placements) of a device in use or operation in addition to the position and orientation shown in the figures. For example, if a device in the figures is inverted, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. The relative proximal and distal directions of surgical instruments are labeled in the figures.

The present disclosure contemplates various cannula mount systems for mounting a cannula to a manipulator arm of a patient side cart of a surgical system. Exemplary embodiments can securely hold cannulas that may vary in size due to a manufacturing tolerance. Exemplary embodiments also may permit cannulas to be mounted and removed in a simple, quick, and reliable manner, for example, enabling one-handed manipulation of latch assemblies used to move a mount between open and closed positions. The exemplary embodiments also facilitate a determination that a cannula has been fully mounted, which minimizes or eliminates occurrences of a user forcing a cannula to be mounted. In various exemplary embodiments, mounting of the cannula may be partially actuated by the cannula mount. Further, the structure of the cannula mount may facilitate proper alignment between a cannula and the mount when mounting the cannula.

Various exemplary embodiments of the present disclosure contemplate cannula mounts for a surgical system. The mount includes a body having an aperture to receive a portion of a cannula. A pivotable clamping arm of the mount may engage the portion of the cannula received in the aperture to clamp the cannula. The clamping arm comprising a cam surface. The mount may further include a block moveable between a first position and a second position. The block may include a cam surface that engages the cam surface of the clamping arm in the first position to actuate the clamping arm to a closed position in which the clamping arm engages the portion of the cannula received in the aperture. The clamping arm may be permitted to move to an open position in which the clamping arm does not engage the cannula when the block is in the second position. The clamping arm may engage and clamp a cannula over a range of motion of the clamping arm, permitting the clamping arm to accommodate cannulas of varying size. The cannula mount may be configured so when the block moves from the second position to the first position, the cam surface of the block engages and slides against the cam surface of the clamping arm until the portion of the cannula is clamped by the clamping arm. The cannula mount may include a single clamping arm or a plurality of clamping arms. When the cannula mount includes a plurality of clamping arms, the block may engage each of the clamping arms in the first position to actuate the clamping arms to the closed position in which the clamping arms engage the portion of the cannula. The clamping arm may be biased to the first position, such as by, for example, a spring. The spring may comprise a plurality of springs to bias the block to the first position. The portion of the cannula may include a metal member and the block may include a magnet to interact with the metal member. The cannula mount may be provided on a manipulator arm of a surgical system, such as a manipulator arm of a patient side cart of a teleoperated surgical system.

Various exemplary embodiments further contemplate a cannula sterile adaptor for a surgical system including a first portion comprising a rigid material and a second portion comprising a compliant material. The cannula sterile adaptor may comprise a depression to receive a clamping arm of a cannula mount of the surgical system. The depression may be located in, for example, the first portion or the second portion of the cannula sterile adaptor. The second portion may be made of a thermoplastic elastomer, such as, for example, a soft, flexible thermoplastic elastomer. According to an exemplary embodiment, a surgical drape may be connected to the second portion. According to another exemplary embodiment, a surgical drape may be connected to the first portion. The first portion may include a retention feature to connect the cannula sterile adaptor to the cannula mount.

Referring now to FIG. 1, an exemplary embodiment of a patient side cart 100 of a teleoperated surgical system is shown. A teleoperated surgical system may further include a surgeon console (not shown) for receiving input from a user to control instruments of patient side cart 100, as well as an auxiliary control/vision cart (not shown), as described in, for example, U.S. Pub. No. US 2013/0325033, entitled "Multi-Port Surgical Robotic System Architecture" and published on Dec. 5, 2013, and U.S. Pub. No. US 2013/0325031, entitled "Redundant Axis and Degree of Freedom for Hardware-Constrained Remote Center Robotic Manipulator" and published on Dec. 5, 2013, each of which is hereby incorporated by reference in its entirety. Non-limiting, exemplary embodiments of teleoperated surgical systems with which the principles of the present disclosure may be utilized include the da Vinci® Si (model no. IS3000) da Vinci® Si Surgical System, Single Site da Vinci® Surgical System, or a da Vinci® Xi Surgical System, available from Intuitive Surgical, Inc. of Sunnyvale, Calif.

Patient side cart 100 may include a base 102, a main column 104, and a main boom 106 connected to main column 104. Patient side cart 100 may also include a plurality of manipulator arms 110, 111, 112, 113, which may each be connected to main boom 106. Manipulator arms 110, 111, 112, 113 may each include an instrument mount portion 120 to which an instrument 130 may be mounted, which is illustrated as being attached to manipulator arm 110. Portions of manipulator arms 110, 111, 112, 113 may be manipulated during a surgical procedure according to commands provided by a user at the surgeon console. In an exemplary embodiment, signal(s) or input(s) transmitted from a surgeon console may be transmitted to the control/vision cart, which may interpret the input(s) and generate command(s) or output(s) to be transmitted to the patient side cart 100 to cause manipulation of an instrument 130 (only one such instrument being mounted in FIG. 1) and/or portions of manipulator arm 110 to which the instrument 130 is coupled at the patient side cart 100.

Instrument mount portion 120 may comprise an actuation interface assembly 122 and a cannula mount 124, with a shaft 132 of instrument 130 extending through cannula mount 124 (and on to a surgery site during a surgical procedure) and a force transmission mechanism 134 of instrument 130 connecting with the actuation interface assembly 122, according to an exemplary embodiment. Cannula mount 124 may be configured to hold a cannula (not shown in FIG. 1) through which shaft 132 of instrument 130 may extend to a surgery site during a surgical procedure. Actuation interface assembly 122 may contain a variety of drive and other mechanisms that are controlled to respond to input commands at the surgeon console and transmit forces to the force transmission mechanism 134 to actuate instrument 130, as those skilled in the art are familiar with.

Although the exemplary embodiment of FIG. 1 shows an instrument 130 attached to only manipulator arm 110 for ease of illustration, an instrument may be attached to any and each of manipulator arms 110, 111, 112, 113. An instrument 130 may be a surgical instrument with an end effector or may be an endoscopic imaging instrument or other sensing instrument utilized during a surgical procedure to provide information, (e.g., visualization, electrophysiological activity, pressure, fluid flow, and/or other sensed data) of a remote surgical site. In the exemplary of FIG. 1, a surgical instrument with an end effector or an imaging instrument may be attached to and used with any of manipulator arms 110, 111, 112, 113. However, the embodiments described herein are not limited to the exemplary embodiment of FIG. 1 and various other teleoperated surgical system configurations may be used with the exemplary embodiments described herein.

Figure 2:
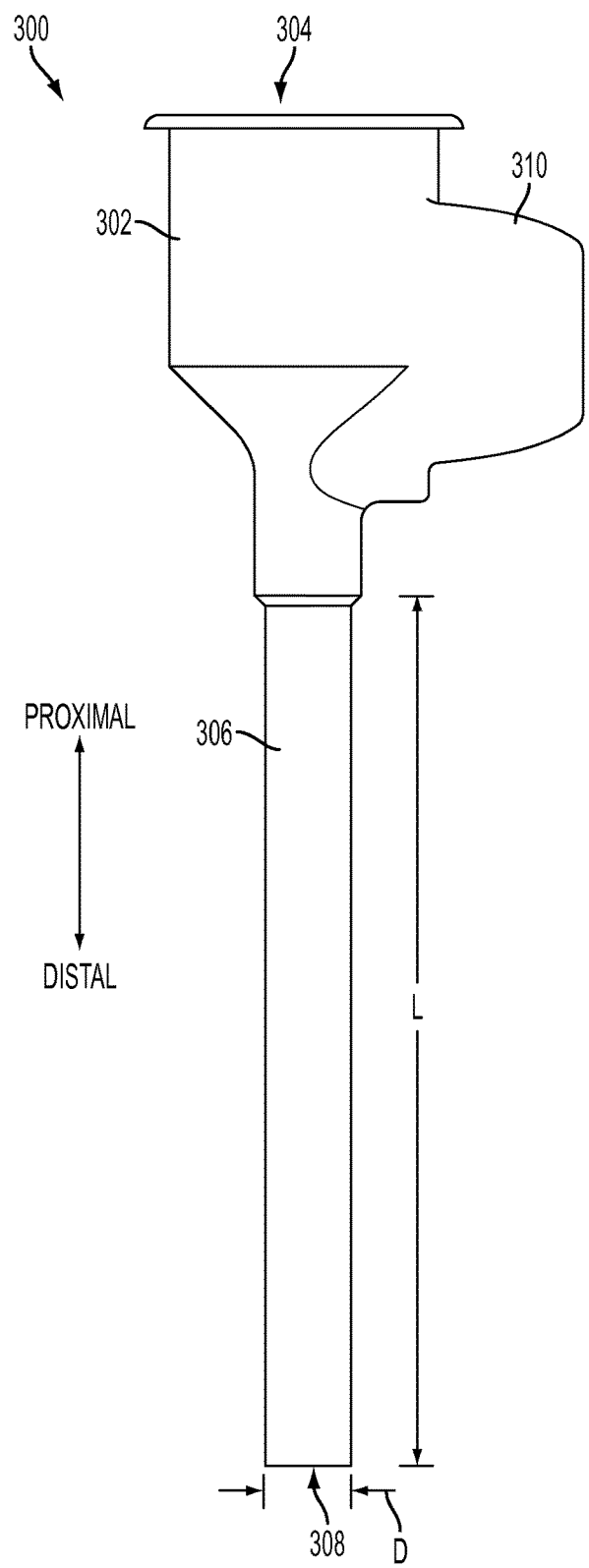
FIG. 2 is a side view of a cannula, according to an exemplary embodiment.

Turning to FIG. 2, a side view of an exemplary embodiment of a cannula 300 is shown. Cannula 300 may include a bowl section 302 forming a proximal end 304 of cannula 300, and a tube 306 extending from bowl section 302 to a distal end 308 of cannula 300. The proximal and distal directions with respect to the orientation of FIG. 2 are labeled. As shown in the exemplary embodiment of FIG. 2, tube 306 may have a length L and distal end 308 may have a diameter D, each of which may vary depending on a desired application of cannula 300, as those having ordinary skill in the art are familiar with. Further, as shown in the exemplary embodiment of FIG. 2, tube 306 may be straight, although the exemplary cannula embodiments described herein are not limited to a straight tube. For example, tube 306 may instead be a curved tube (e.g. a tube having a curved longitudinal axis along all or part of its length). According to an exemplary embodiment, tube 306 may be rigid. However, the various exemplary embodiments described herein are not limited to cannula with rigid tubes. For example, tube 306 may be, for example, a flexible tube.

Cannula 300 may be inserted through an opening in a patient's body to a surgical site. For example, distal end 308 of cannula may be inserted through an opening, such as, for example, an incision, natural orifice, or port, to a surgical site. A surgical instrument, such as instrument 160 in the exemplary embodiment of FIG. 1, can be inserted through cannula 300 to the surgical site. For example, an instrument may be inserted into proximal end 304 of cannula and advanced through bowl section 302, tube 306, and distal end 308 of cannula 300 to a surgical site.

According to an exemplary embodiment, cannula 300 may be attached to a cannula mount to connect the cannula to a manipulator arm of a patient side cart, such as cannula mount 124 of a manipulator arm 110, 111, 112, or 113 of patient side cart 100 of the exemplary embodiment of FIG. 1. As depicted in FIG. 2, cannula 300 may include an attachment portion 310 to connect cannula 300 to a cannula mount of a manipulator arm. Attachment portion 310 may be, for example, a projection that is configured to be inserted into and held by a cannula mount of a manipulator arm, according to an exemplary embodiment. As shown in the exemplary embodiment of FIG. 2, attachment portion 310 may be part of, or otherwise joined to, bowl section 302 of cannula 300 and may project from bowl section 302. As will be discussed below, a cannula sterile adaptor (not shown in FIG. 2) may be mounted between a cannula mount and cannula 300, with cannula sterile adaptor being connected to a drape (not shown in FIG. 2) so the cannula sterile adaptor and the drape may form a boundary between a sterile region and non-sterile region.

Figure 3:
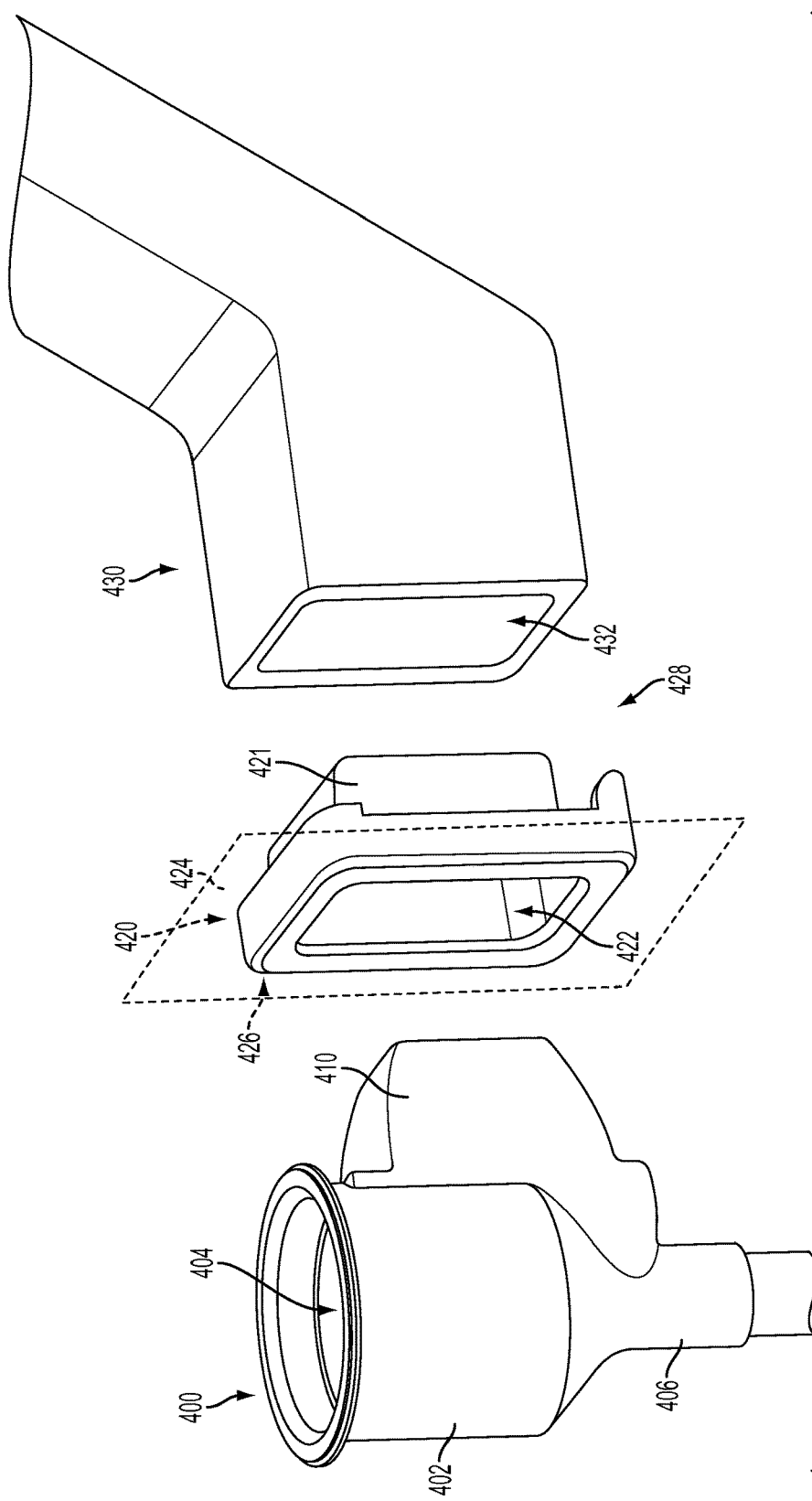
FIG. 3 is an exploded schematic view of parts of a cannula mount system, according to an exemplary embodiment.

To schematically explain the mounting of a cannula and cannula sterile adaptor to a manipulator arm of a patient side cart, FIG. 3 depicts an exploded view of a cannula 400, cannula sterile adaptor 420, and a cannula mount 430 of a patient side cart. Cannula mount 430 may be, for example, cannula mount 124 provided on one of manipulator arms 110-113 of patient side cart 100 of FIG. 1. Cannula 400 may include a bowl section 402, proximal end 404, tube 406, and attachment portion 410, similar to cannula 300 in the exemplary embodiment of FIG. 2. Cannula sterile adaptor 420 may be joined to cannula mount 430, such as by inserting a portion 421 of cannula sterile adaptor 420 into an aperture 432 of cannula mount 430. As those having ordinary skill in the art are familiar with, cannula sterile adaptor 420 may facilitate forming a boundary between a sterile region and non-sterile region. For example, a surgical drape 426 (shown schematically in FIG. 3 with dashed lines) may be attached to cannula sterile adaptor 420 to separate a sterile side 426 from a non-sterile side 428 of drape 424. Attachment portion 410 of cannula 400 may be structured to fit inside an opening 422 of cannula sterile adaptor 420 so that cannula 400 remains on sterile side 426 of drape 424. Further, when cannula sterile adaptor 420 has been connected to cannula mount 430, and attachment portion 410 is inserted into opening 422 of cannula sterile adaptor 420, cannula 400 may also be connected to cannula mount 430 so that cannula 400 may be held by cannula mount 430 during a surgical procedure.

According to an exemplary embodiment, a portion of cannula tube 406 may be inserted into a patient's body, such as via an orifice, before mounting cannula 400 to cannula mount 430. In this case, cannula sterile adaptor 420 may be first mounted to cannula mount 430 and then the manipulator arm including cannula mount 430 may be maneuvered so aperture 432 of cannula mount 430 is aligned with attachment portion 410. Subsequently, the manipulator arm including cannula mount 430 and the attachment portion 410 may be maneuvered toward each other so attachment portion 410 is inserted within aperture 432, with sterile adaptor 420 disposed therebetween, to mount cannula 400 to cannula mount 430. Although the exemplary embodiment of FIG. 3 depicts cannula 400 as being mounted to cannula mount 430 with cannula sterile adaptor 420, cannula 400 may be mounted directly to cannula mount 430 without cannula sterile adaptor 420 in between cannula 400 and cannula mount 430.

Figure 4:
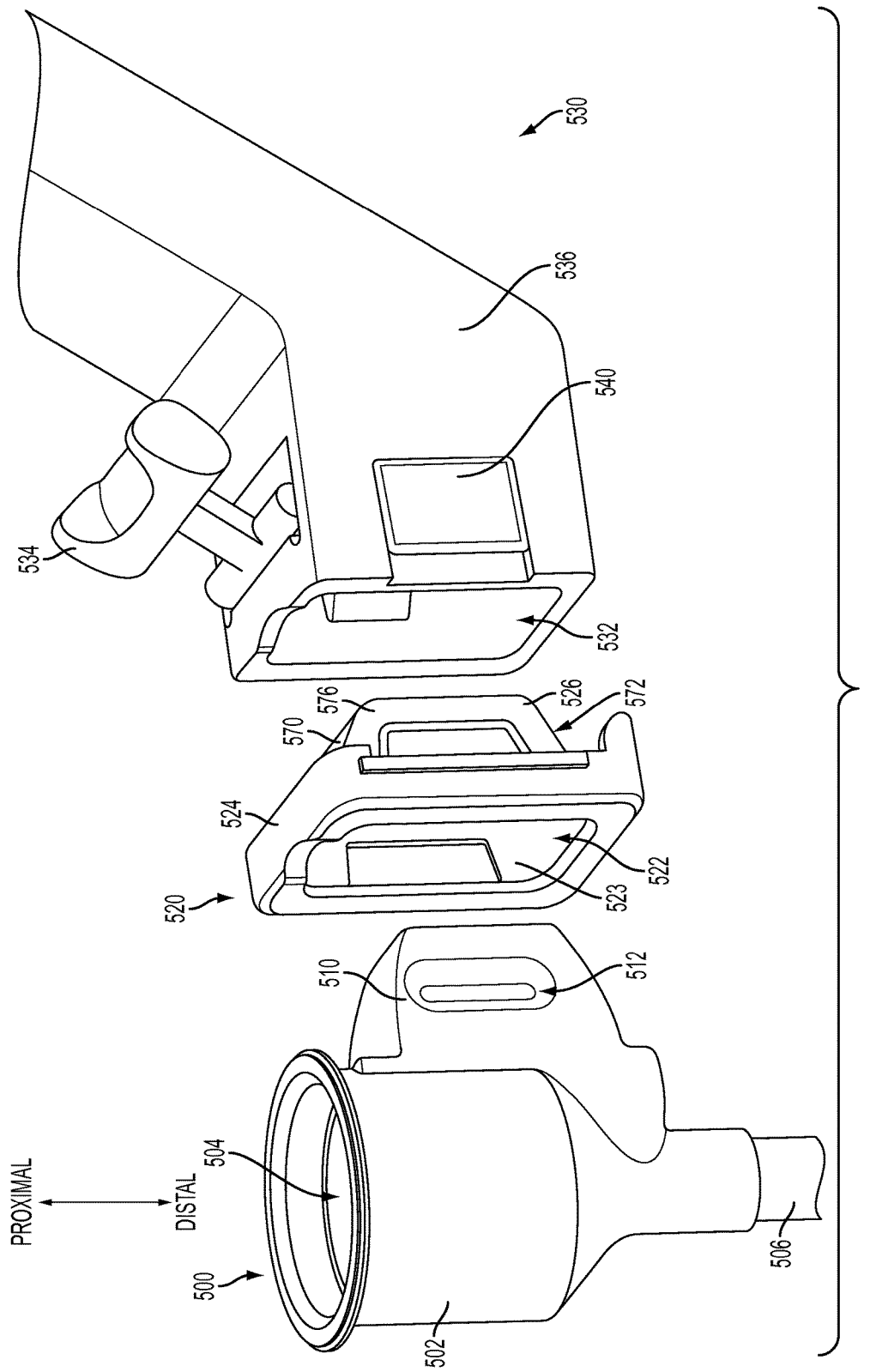
FIG. 4 is an exploded view of a cannula mount system, according to an exemplary embodiment.
Figure 5:
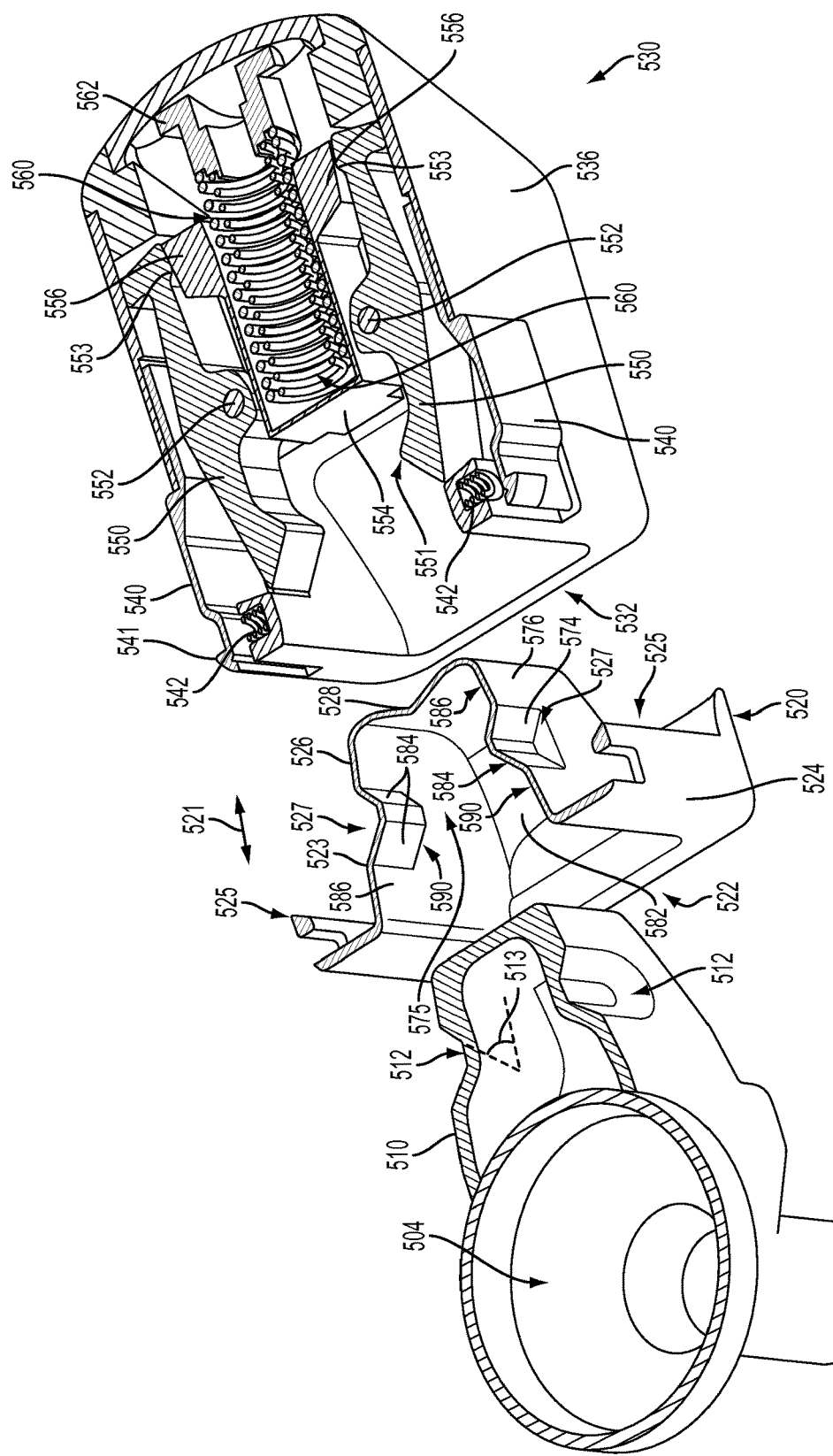
FIG. 5 is a partial perspective, transverse sectional view of the cannula mount system of FIG. 4.

It is desirable to provide structures for mounting cannulas, as well as cannula sterile adaptors, in a quick, easy, and reliable manner that also securely hold the cannula. Various exemplary embodiments are contemplated for achieving this. Turning to FIG. 4, an exploded view is shown of an exemplary embodiment of a cannula 500, cannula sterile adaptor 520, and a cannula mount 530 of a patient side cart. Cannula mount 530 may be, for example, cannula mount 124 provided on one of manipulator arms 110-113 of patient side cart 100 of FIG. 1. Cannula 500 may include a bowl section 502, proximal end 504, tube 506 (shown in part in the exemplary embodiment of FIG. 4), and attachment portion 510, similar to cannula 300 in the exemplary embodiment of FIG. 2. According to an exemplary embodiment, attachment portion 510 may include depressions 512, such as on opposite sides of attachment portion 510 (as shown in FIG. 5), to assist with mounting cannula 500 to cannula mount 530, as will be discussed below. Depressions 512 may be configured to facilitate mounting of cannula 500 to cannula sterile adaptor 520 and cannula mount 530. For example, an angle 513 of depressions 512 may be selected to facilitate an application of a large amount of force between attachment portion 510, cannula sterile adaptor 520, and cannula mount 530 when cannula 500 is mounted, but also facilitate release of attachment portion 510. According to an exemplary embodiment, angle 513 may range from, for example, about 50 degrees to about 60 degrees.

According to an exemplary embodiment, angle 513 may be, for example, about 40 degrees.

Cannula sterile adaptor 520 may include an aperture 522 to receive attachment portion 510 of cannula 500. As discussed above in regard to FIG. 3, cannula sterile adaptor 520 may be attached to a surgical drape (not shown in FIG. 4) to facilitate forming a boundary between a sterile region and a non-sterile region. In various exemplary embodiments, cannula sterile adaptor 520 may be provided with different properties for different portions (regions) to facilitate mounting of the cannula sterile adaptor 520 and/or cannula 500 to cannula mount 530. For example, cannula sterile adaptor 520 may include a first portion 524 and a second portion 526 that have differing properties, as explained in more detail below.

According to an exemplary embodiment, first portion 524 may be made of a relatively rigid material that provides structural support for cannula sterile adaptor 520 when cannula sterile adaptor 520 is mounted to cannula mount 530, as well as for cannula 500 when cannula 500 is mounted to cannula sterile adaptor 520. The relatively rigid material may also facilitate alignment of attachment portion 510 of cannula 500 when attachment portion 510 is inserted within aperture 522 of cannula sterile adaptor 520, due to the stiffness and rigidity of first portion 524. Further, the relatively rigid material can be a smooth, low friction material, which may facilitate alignment and insertion of cannula 500 into cannula sterile adaptor 520 by providing a low friction surface over which attachment portion 510 of cannula 500 may easily slide. In addition, first portion 524 may be configured to accommodate forces applied between cannula 500 and cannula mount 530, such as clamping forces and body wall forces, when cannula 500 is mounted to cannula mount 530.

First portion 524 may be made of a plastic material, such as, for example, polycarbonate, acrylonitrile butadiene styrene (ABS), polycarbonate/ABS, polyurethane, and other plastics familiar to one of ordinary skill in the art. The low friction surface may also assist with latching the cannula 500 to cannula mount 530 by facilitating sliding of cannula 500 when a latching force supplied by cannula mount 530 draws cannula 500 into a mounting position during latching. According to an exemplary embodiment, cannula sterile adaptor 520 may be treated with a lubricant to facilitate insertion and/or removal of cannula 500. The lubricant may be, for example, a dry coating of polytetrafluoroethylene (PTFE) or other lubricant familiar to one of ordinary skill in the art that is applied to a surface of cannula sterile adaptor 520. In another example, a lubricant filler may be added to the material of cannula sterile adaptor 520, such as to the material of first portion 524 and/or second portion 526. The lubricant filler may be, for example, silicone oil, PTFE, or other lubricant filler familiar to one of ordinary skill in the art. First portion 524 may be, for example, the part of cannula sterile adaptor 520 that is connected to a surgical drape (not shown in FIG. 4), as described above with regard to FIG. 3, with a sterile region on the side of the drape facing cannula 500 and the non-sterile region on the side of the drape facing cannula mount 530.

In various exemplary embodiments, a sterile adaptor can have a configuration, including size, shape, and/or surface profiles and features that facilitate its interaction with both the cannula mount and the cannula. As will be further explained below with reference to the illustrated exemplary embodiments, such configurations can promote the ease in which a user can insert the cannula and cannula adapter into the cannula mount and/or promote the stability of the attachment of the various pieces.

According to an exemplary embodiment, aperture 522 of cannula sterile adaptor 520 forms an opening in cannula sterile adaptor 520 having a shape corresponding to the shape of attachment portion 510 of cannula 500, such as to facilitate mounting of cannula 500 within cannula sterile adaptor 520. For example, the cannula sterile adaptor 520 has a sidewall 523 that surrounds a recess 575 extending into cannula sterile adaptor 520 from the opening formed by aperture 522. According to an exemplary embodiment, attachment portion 510 tapers in a direction away from the bowl section 502. For example, the recess 575 and surrounding sidewall 523 can taper along direction 521 in FIG. 5, for example in a direction toward the direction of insertion of the sterile adaptor 520 into the cannula mount 530. Further, as shown, the recess 575 and sidewall 523 can be slightly elongated in the direction of insertion, with the recess 575 having a shape corresponding to the shape of attachment portion 510 of cannula 500 and the outer surface profile of the sidewall 523 having a shape generally corresponding to the space in which the sterile adaptor 520 is received within the cannula mount 530.

Figure 26:
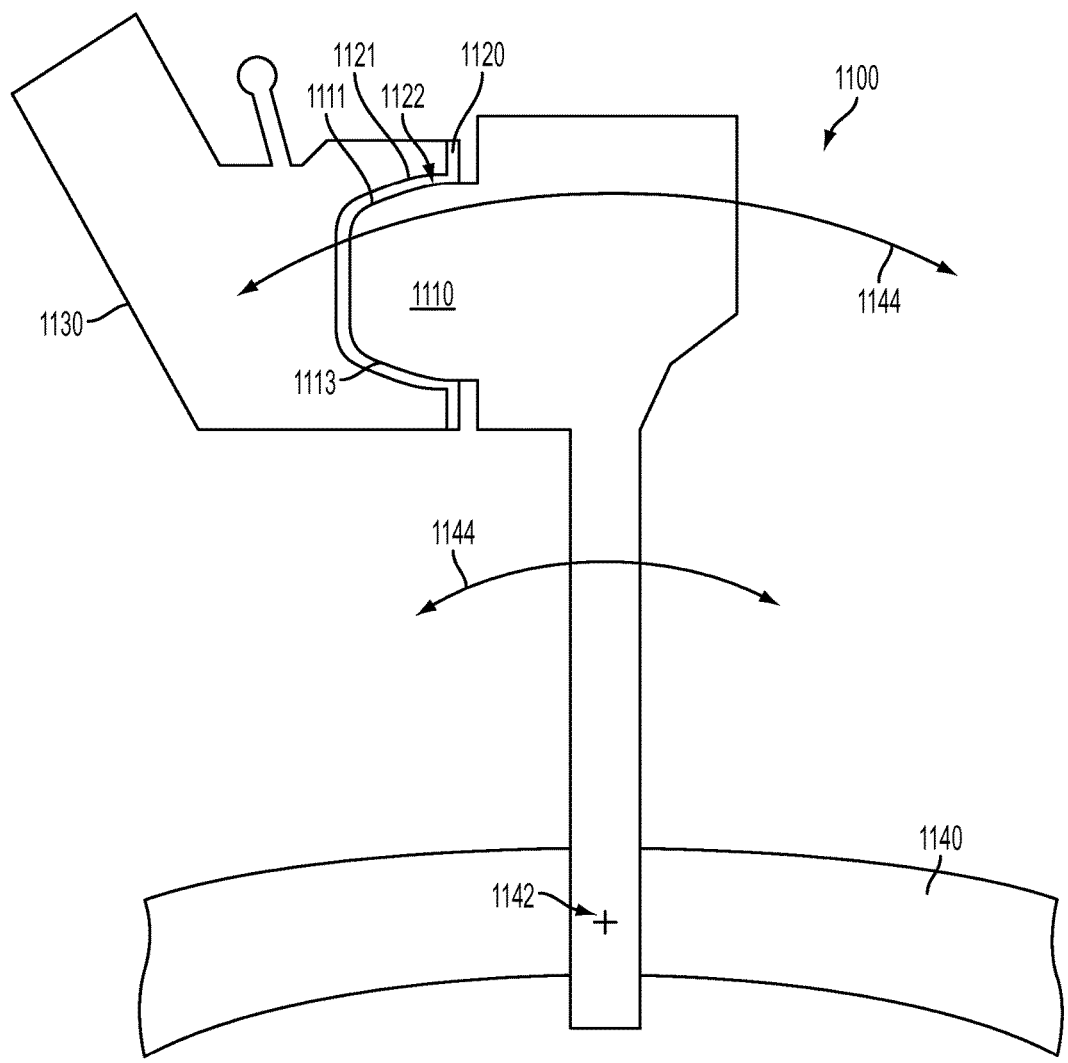
FIG. 26 is a partial side view of a cannula inserted into a body wall, according to another exemplary embodiment.

Further, as will also be discussed below with regard to FIG. 26, a proximal surface and a distal surface of a cannula attachment portion may taper. With reference to FIG. 4, the outer surfaces of the sidewall 523 may be rounded and taper to assist in insertion of the cannula adaptor 520 into the cannula mount 530. For example, proximal outer surface 570 and distal outer surface 572 (the directions being considered relative to the direction in which the cannula is extending in the view of FIG. 4, such as proximal-distal direction in FIG. 4) of sidewall 523 of cannula sterile adaptor 520 may be tapered, as depicted in FIG. 4. Further, generally oppositely facing side outer surfaces 576 (only one such surface being visible in FIG. 4) may taper and cooperate with surfaces 570 and 572 to form four sides of recess 575 so recess 575 corresponds in shape to the shape of attachment portion 510. Sidewall 523 may further include inner surfaces corresponding to outer surfaces 570, 572, 576, such as a distal inner surface 582, a proximal inner surface (not shown but generally facing distal inner surface 582), and inner side surfaces 586, as depicted in FIG. 5. Inner surfaces may taper, such as in a manner similar to outer surfaces 570, 572, 576, and form four sides of recess 575 so recess 575 corresponds in shape to the shape of attachment portion 510. According to an exemplary embodiment, inner surfaces of sidewall 523 may provide recess 575 with a square frustum shape. Therefore, the sidewall 523 that forms recess 575 may include four inner surfaces (e.g., a first pair of inner surfaces that generally face each other, such as the distal inner surface 582 and the proximal inner surface, and a second pair of two generally oppositely facing pairs of surfaces) that taper along direction 521, as depicted in FIGS. 4 and 5. The outer surfaces of sidewall 523 may also taper along direction 521, as depicted in FIGS. 4 and 5. Outer surfaces of sidewall 523 may also provide cannula sterile adaptor 520 with a square frustum shape, such as in second portion 526 of cannula sterile adaptor 520. The inner and/or outer surfaces of sidewall 523 of cannula sterile adaptor 520 may be curved or flat (e.g., linear) in shape, such as to provide the tapered shape of cannula sterile adaptor 520, which facilitates insertion of cannula sterile adaptor 520 into mount 530 and cannula attachment portion 510 into the recess 575 of cannula sterile adaptor 520. Further, the inner surfaces of sidewall 523 may form two pairs of generally oppositely disposed tapering surfaces, the surfaces of each pair facing generally toward each other.

Cannula sterile adaptor 520 may include depressions or other similar surface features to assist with mounting cannula 500 to cannula mount 530, as will be discussed below. According to an exemplary embodiment, the outer surfaces 576 of sidewall 523 include depressions 527. A depression 527 may be, for example, located on each of the opposite outer surfaces 576 of cannula sterile adaptor 520 (as shown in the exemplary embodiment of FIG. 5). Depressions 527 may be formed by, for example, one or more curved surfaces or may be formed by a plurality of flat, linear surfaces, as illustrated in FIG. 5. Depressions 527 may generally correspond in shape to tips of clamping arms of mount 530, which will be discussed below. Thus, the sidewall 523, which forms recess 575 having a shape corresponding to a shape of attachment portion 510, may further include depressions 527 corresponding in shape According to an exemplary embodiment, inner surfaces (e.g., inner side surfaces 586) of sidewall 523 include protrusions 590 extending into recess 575. The protrusions 590 may correspond in shape to depressions 512 in attachment portion 510 of cannula 500. Protrusions 590 may correspond in location and/or shape to depressions 527, such as via protrusions 590 being located on an opposite side of sidewall 523 from depression 527. Protrusions 590 may be formed by, for example, one or more curved surfaces or may be formed by a plurality of flat, linear surfaces 584, as illustrated in FIG. 5. Flat surfaces 584 of protrusions 590 may be angled at substantially the same angle 513 as depressions 512 of attachment portion 512 in order to correspond in shape to attachment portion 510. Flat surfaces of depressions 527 (e.g., surfaces 574) may similarly be angled at substantially the same angle 513 as depressions 512 of attachment portion 512, according to an exemplary embodiment.

The depressions and protrusions depicted in the drawings are exemplary in nature and the present disclosure contemplates other configurations of depressions and protrusions, such as, for example, other numbers of depressions and/or protrusions and other geometries for depressions and/or protrusions. Further, other surface features could be provided in a cannula sterile adaptor to mate with complementary features of a cannula mount and/or attachment portion of a cannula, such as to provide a secure engagement between the mount, cannula sterile adaptor, and cannula.

Figure 29:
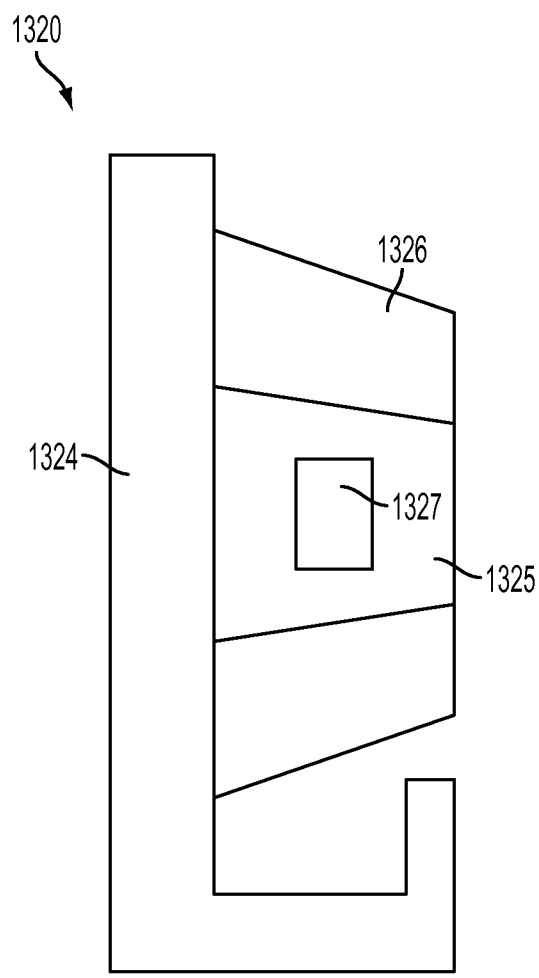
FIG. 29 is a side view of a cannula sterile adaptor, according to another exemplary embodiment.

According to an exemplary embodiment, first portion 524 of cannula sterile adaptor 520 may comprise sidewall 523, and thus depressions 527, as well as protrusions 590. Turning to FIG. 29, a side view of an exemplary embodiment of a cannula sterile adaptor 1320 is shown that includes a first portion 1324 and a second portion 1326. First portion 1324 may be made of, for example, a relatively rigid material and second portion 1326 may be made of, for example, a relatively compliant material, as discussed in the various exemplary embodiments herein. According to an exemplary embodiment, first portion 1324 may include one or more projections 1325 comprising a depression 1327 to assist with mounting a cannula to a cannula mount, as discussed above with regard to the exemplary embodiment of FIG. 5. Thus, although the exemplary embodiment of FIG. 5 depicts first portion 524 as lacking projections (and second portion 526 of cannula sterile adaptor 520 forming depressions 527) a first portion of a cannula sterile adaptor may have other configurations, including the configuration of FIG. 29 that includes one or more projections 1325. First portion 1324 may include, for example, a plurality of projections 1325 comprising a depression 1327, such as a pair of projections on lateral sides of cannula sterile adaptor 1320. According to an exemplary embodiment, second portion 1326 may be connected to projection 1325, such as, for example, over-molding second portion 1326 to projection 1325.

According to an exemplary embodiment, second portion 526 of cannula sterile adaptor 520 may be made of a relatively compliant material. The relatively compliant material may permit second portion 526 to elastically deform with relative ease while also providing a seal to maintain a boundary between a sterile region and a non-sterile region. For example, second portion 526 may be the part of cannula sterile adaptor 520 that is connected to a surgical drape (not shown in FIG. 4), as described above with regard to FIG. 3, with a sterile region on the side of the drape facing cannula 500 and the non-sterile region on the side of the drape facing cannula mount 530. According to an exemplary embodiment, second portion 526 may be made of a plastic material overmolded onto first portion 524. Second portion 526 may be made of, for example, a thermoplastic elastomer (TPE), thermoplastic polyurethane (TPU), or other plastic material familiar to one of ordinary skill in the art. According to an exemplary embodiment, second portion 526 of cannula sterile adaptor 520 may include depressions 527 (as well as corresponding protrusions 590), such as on opposite sides of second portion 526 (as shown in the exemplary embodiment of FIG. 5), to assist with mounting cannula 500 to cannula mount 530, as will be discussed below.

Cannula sterile adaptor 520 may include structures to facilitate deformation of cannula sterile adaptor 520, such as when cannula 500 is inserted into and withdrawn from cannula sterile adaptor 520. According to an exemplary embodiment, second portion 526 of cannula sterile adaptor 520 may include a bellows structure 528, as shown in FIG. 5, to facilitate deformation of second portion 526. Second portion 526 of cannula sterile adaptor 520 may include a relatively thin sidewall 523 to permit deformation of second portion 526, in addition to or without bellows structures 528. Although bellows structure 528 and thin sidewall 523 have been discussed in regard to cannula sterile adaptor 520 of the exemplary embodiment of FIG. 5, bellows structure 528 and/or thin sidewall 523 may be used in a cannula sterile adaptor that is made of a single material instead of a first portion 524 and second portion 526, according to an exemplary embodiment.

As discussed above, cannula mount 530 may include features to engage a cannula sterile adaptor. Turning to FIG. 5, cannula 500, cannula sterile adaptor 520, and cannula mount 530 are shown so as to reveal internal structures. According to an exemplary embodiment, cannula mount 530 may include one or more retention features 541 that engage with complementary retention features 525 of cannula sterile adaptor 520. Retention features 525 may be molded as one piece with first portion 524 of cannula sterile adaptor 520, according to an exemplary embodiment, or may be provided as a separate piece joined to first portion 524. Retention features 541 of cannula mount 530 may be arranged to move relative to a body 536 of cannula mount 530, such as when cannula sterile adaptor 520 is mounted to cannula mount 530. For instance, a retention feature 541 may be biased into an engaged position, such as via a spring 542. Thus, when cannula sterile adaptor 520 is mounted to cannula mount 530, a retention feature 525 of cannula sterile adaptor 520 may engage a retention feature 541 of cannula mount 530, initially causing retention feature 541 and spring 542 to be depressed until complementary retention features 525 and 541 are fully engaged. In this fully engaged position, spring 542 biases retention feature 541 to the engaged position to mount cannula sterile adaptor 520 to cannula mount 530. To disconnect cannula sterile adaptor 520, retention feature 541 may be depressed against the biasing force of spring 542, such as by depressing a release mechanism 540 of retention feature 541. As shown in FIG. 4, release mechanism 540 may be exposed on an exterior surface of body 536 of cannula mount 530. As shown in the exemplary embodiment of FIG. 5, cannula sterile adaptor 520 and cannula mount 530 may each include two pairs of corresponding retention features 525 and 541, with retention features 525 and 541 on opposing sides of cannula sterile adaptor 520 and cannula mount 530, although the various embodiments described herein contemplate other numbers of corresponding retention feature pairs 525 and 541, such as, for example, one, three, four, or more numbers of pairs.

Cannula mount 530 may include various structures to mount cannula 500 in a secure and reliable manner that is also easy to use. As shown in FIG. 5, cannula mount 530 may include a pair of clamping arms 550 to engage cannula 500. For example, when attachment portion 510 of cannula 500 is inserted into aperture 532 of cannula mount 530, tips 551 of clamping arms 550 may latch to depressions 512 of attachment portion 510 to mount cannula 500 to cannula mount 530. Further, if cannula sterile adaptor 520 is mounted to cannula mount 530, attachment portion 510 may be inserted within aperture 522 of cannula sterile adaptor 520 and tips 551 of clamping arms 550 may engage depressions 527 of cannula sterile adaptor 520 (or depressions 1327 of cannula sterile adaptor 1320 of the exemplary embodiment of FIG. 29). Because second portion 526 is relatively compliant, a portion of cannula sterile adaptor 520, such as part of second portion 526 (e.g., when section portion 526 forms depressions 527), may in turn be compressed by clamping arms 550 into depressions 512 of attachment portion 510 to mount cannula 500 to cannula mount 530.

Clamping arms 550 may be actuated to pivot about pins 552 to facilitate mounting and releasing cannula 500. According to an exemplary embodiment, clamping arms 550 may be actuated by a moveable block 554 that engages and moves clamping arms 550 into the closed (latched) position shown in FIG. 5. For example, block 554 may include a cam surface 556 that engages each of clamping arms 550, such as a cam follower surface 553 of clamping arms 550, causing clamping arms 550 to pivot to the closed position shown in FIG. 5.

Moveable block 554 may include a device to bias moveable block 554 into a closed (i.e., locked) position, such as the position shown in FIG. 5, to securely latch cannula 500 to cannula mount 530 with clamping arms 550. According to an exemplary embodiment, a spring 560 may bias moveable block 554 in the position shown in FIG. 5. Spring 560 may be connected between a mounting block 562 and moveable block 554, although the various embodiments described herein are not limited to this structure and spring 560 may be instead connected between body 536 of cannula mount 530 and moveable block 554. According to an exemplary embodiment, cannula mount 530 may include a sensor to detect the position of moveable block 554 to infer whether spring 560 has been depressed and whether clamping arms 550 are in a locked or released position. The sensor, for example, may be a switch that moveable block 554 contacts as moveable block 554 is actuated back and forth to actuate clamping arms 550. Output from the sensor may be transmitted to a controller of a surgical system to provide feedback, for example, whether clamping arms 550 are in a locked or released position.

Figure 6:
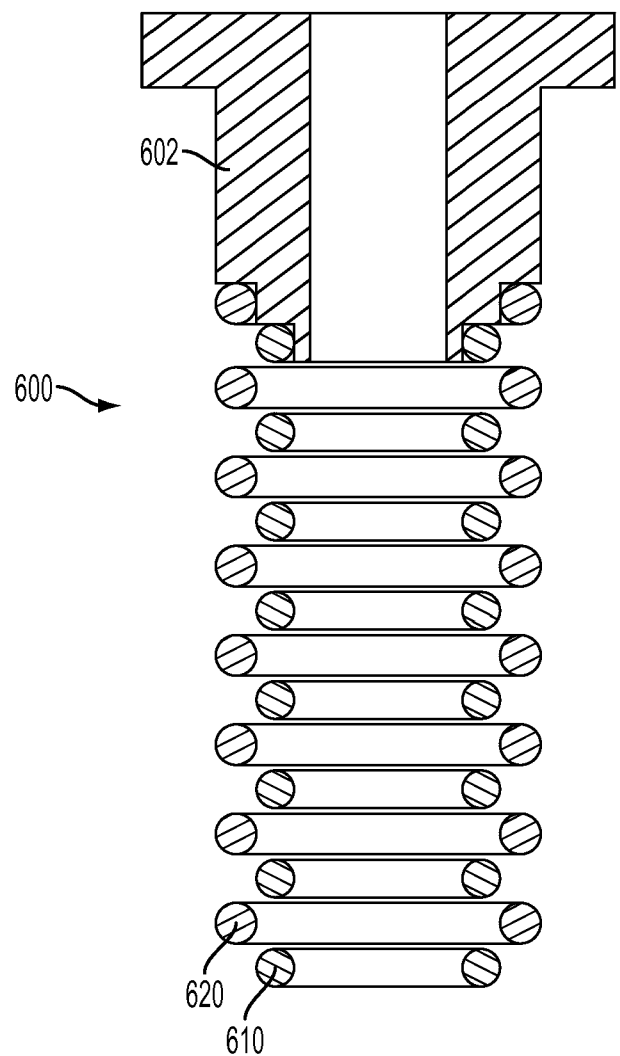
FIG. 6 is a sectional view of a nested spring, according to an exemplary embodiment.

Spring 560 may be a coil spring or other type of spring familiar to one of ordinary skill in the art, according to an exemplary embodiment. Although spring 560 may be a single spring, spring 560 may instead include a plurality of springs. For instance, because the force exerted by a spring varies in proportion to the distance the spring is deformed from its equilibrium length, spring 560 may include a plurality of springs of different types (e.g., different spring constants) to provide a high and substantially constant force over the distance spring 560 is deformed. Turning to FIG. 6, an exemplary embodiment of a nested spring 600 is shown that may be used for spring 560. Nested spring 600 includes a first spring 610 located within a second spring 620. Nested spring 600 may be connected to a mounting block 602, such as mounting block 562 of FIG. 5, or may be mounted to a body 536 of cannula mount 530. First and second springs 610 and 620 may differ in material and/or geometry to provide different spring constants so that overall nested spring 600 provides a relatively high and substantially constant force over the distance nested spring 600 is deformed, such as when nested spring 600 is compressed.

Cannula mount 530 may include a mechanism for a user to actuate a cannula latch assembly including moveable block 554 and clamping arms 550. As shown in FIG. 4, cannula mount 530 may include a handle 534 to actuate moveable block 554. According to an exemplary embodiment, a single handle 534 may be provided to facilitate mounting and releasing of a cannula. According to an exemplary embodiment, handle 534 may be provided as a single mechanism for a user to use to actuate moveable block 554 and thus both of clamping arms 550. Handle 534 may enable a user to actuate the moveable block 554, and thus clamping arms 550 with one hand, thus enabling the user to manipulate cannula 500 with a second hand.

Figure 7:
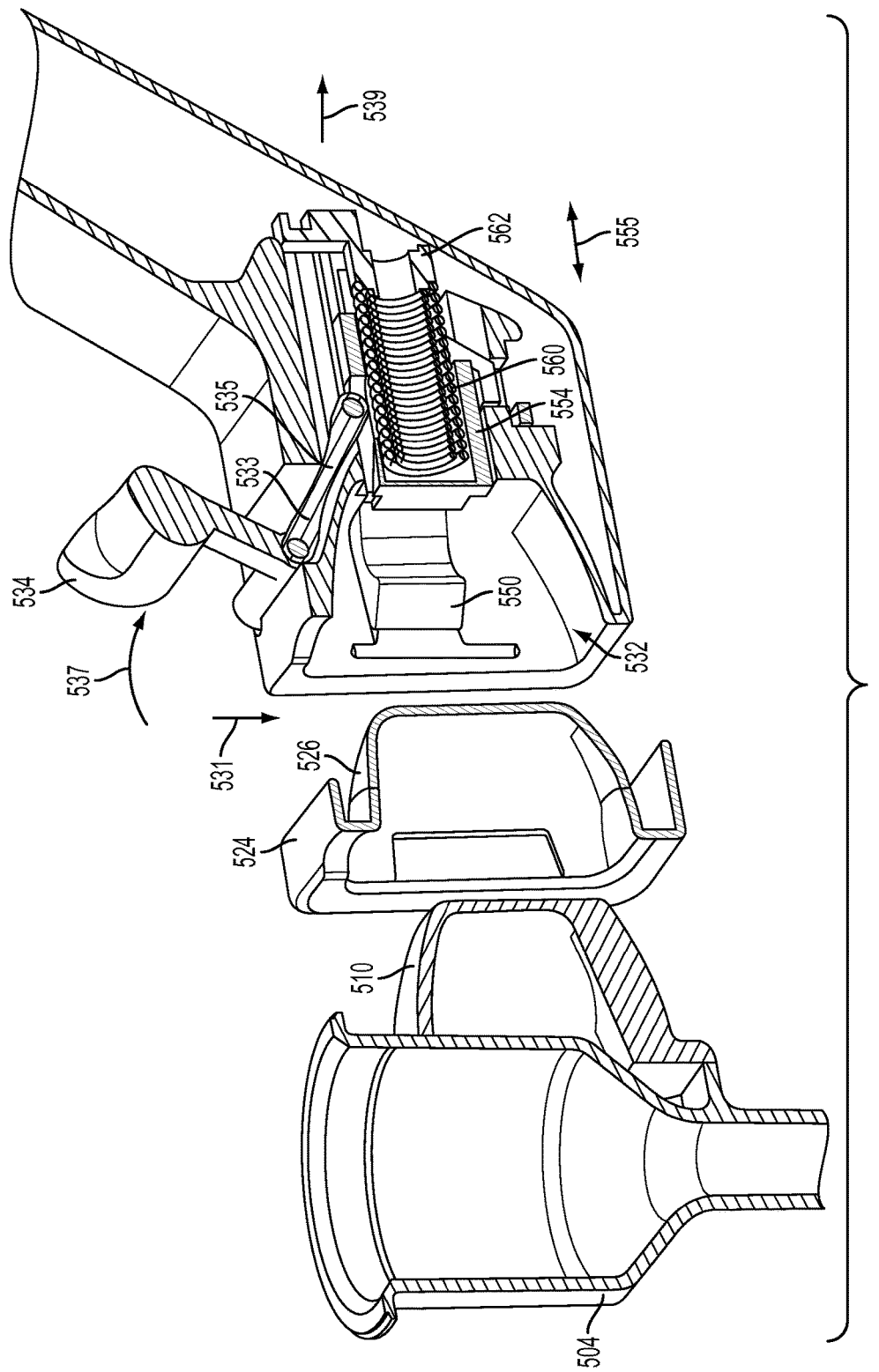
FIG. 7 is a partial perspective, lengthwise sectional view of the cannula mount system of FIG. 4.

Handle 534 may actuate moveable block 554 via a connection between handle 534 and moveable block 554. Turning to FIG. 7, which shows a cross-sectional view of cannula 500, cannula sterile adaptor 520, and cannula mount 530 from the side. As shown in FIG. 7, handle 534 may be connected to moveable block 554 via a link 535, according to an exemplary embodiment. When handle 534 is depressed in the direction indicated by arrow 537 in FIG. 7, link 535 and moveable block 554 are moved along direction 539 in FIG. 7. As will be discussed below, when moveable block 554 is moved along direction 539, clamping arms 550 are moved to an open position to permit cannula 550 to be mounted or released.

According to an exemplary embodiment, link 535 may connect handle 534 to moveable block 554 such that when handle 534 is depressed in direction 537 in FIG. 7, link 535 will begin to align with a long axis 555 of moveable block 554 as link 535 moves in direction 539 and a portion 533 of link 535 connected to handle 534 moves downward along direction 531. As a result, when handle 534 is initially moved along direction 537 in FIG. 7, a force needed to actuate handle 534 initially increases with the increasing spring force but subsequently decreases, such as when substantial alignment occurs between link 535 and long axis 555 of moveable block 554 and the angle between handle 534 and link 535 decreases. As a result, once handle 534 is fully depressed, the handle 534 may remain in the fully depressed position because a reduced amount of force is required to do so, which in turn may permit a user to focus on inserting and aligning cannula 500 within cannula mount 530, or removing cannula 500 from cannula mount 530.

Figure 8:
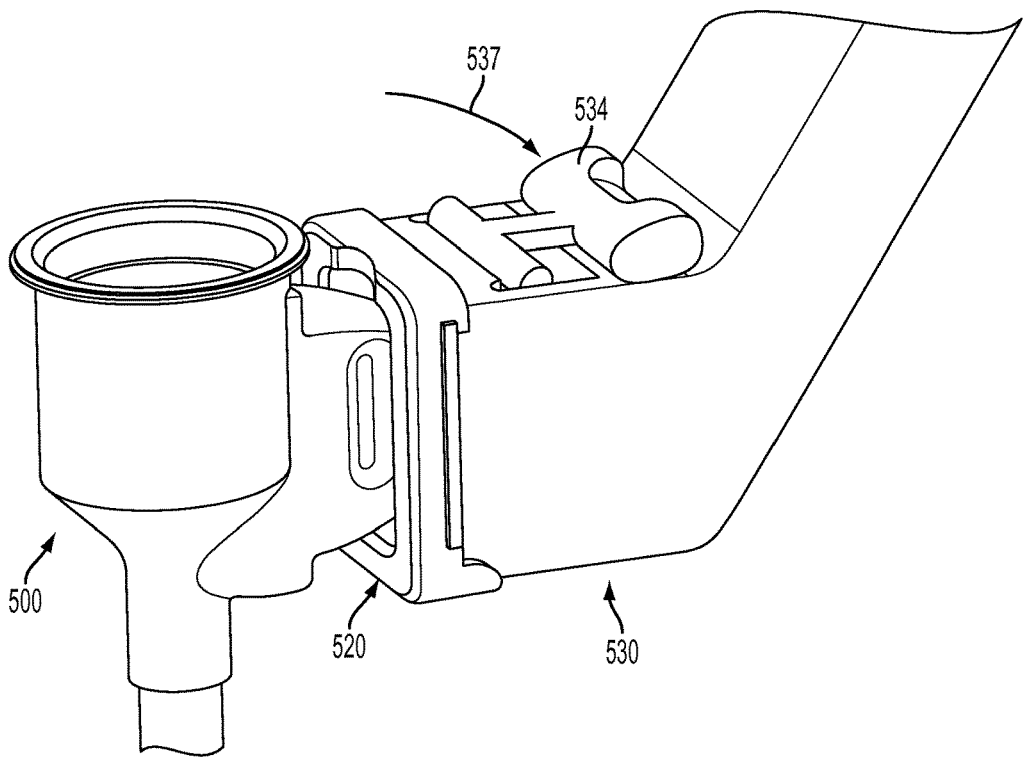
FIG. 8 shows a perspective view of the cannula mount system of FIG. 4 with a handle in a depressed position.
Figure 9:
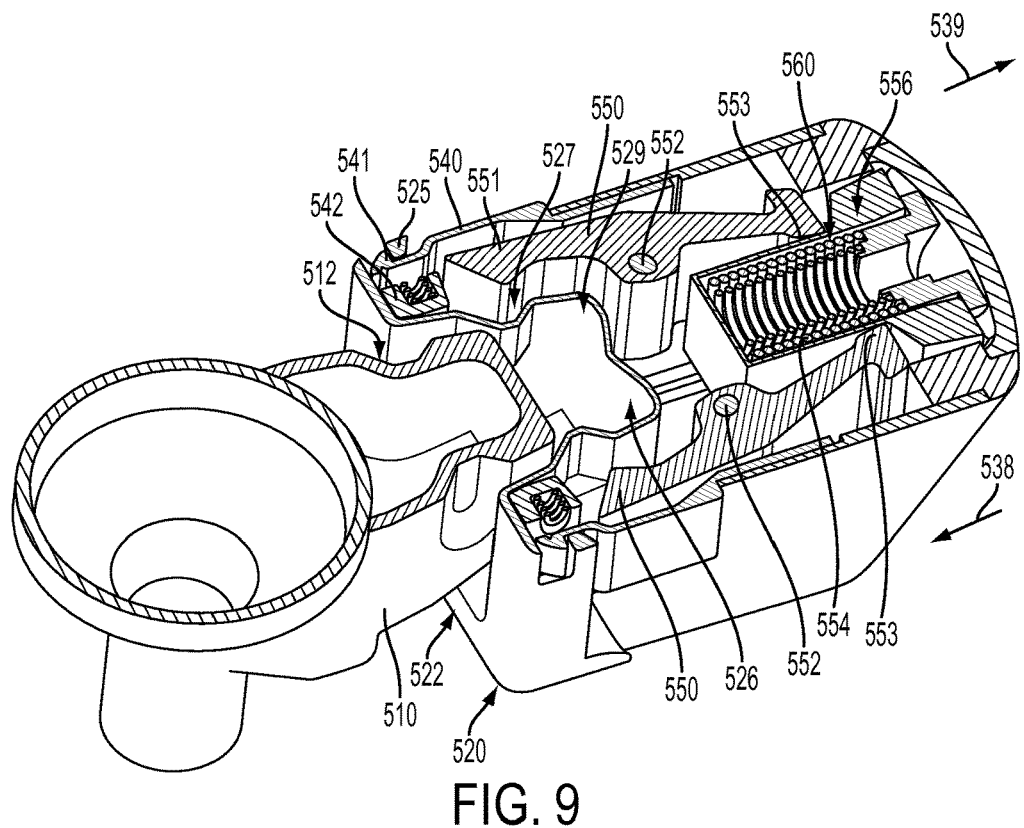
FIG. 9 shows the cannula mount system of FIG. 4 with clamping arms in an open position and the cannula partially inserted.
Figure 10:
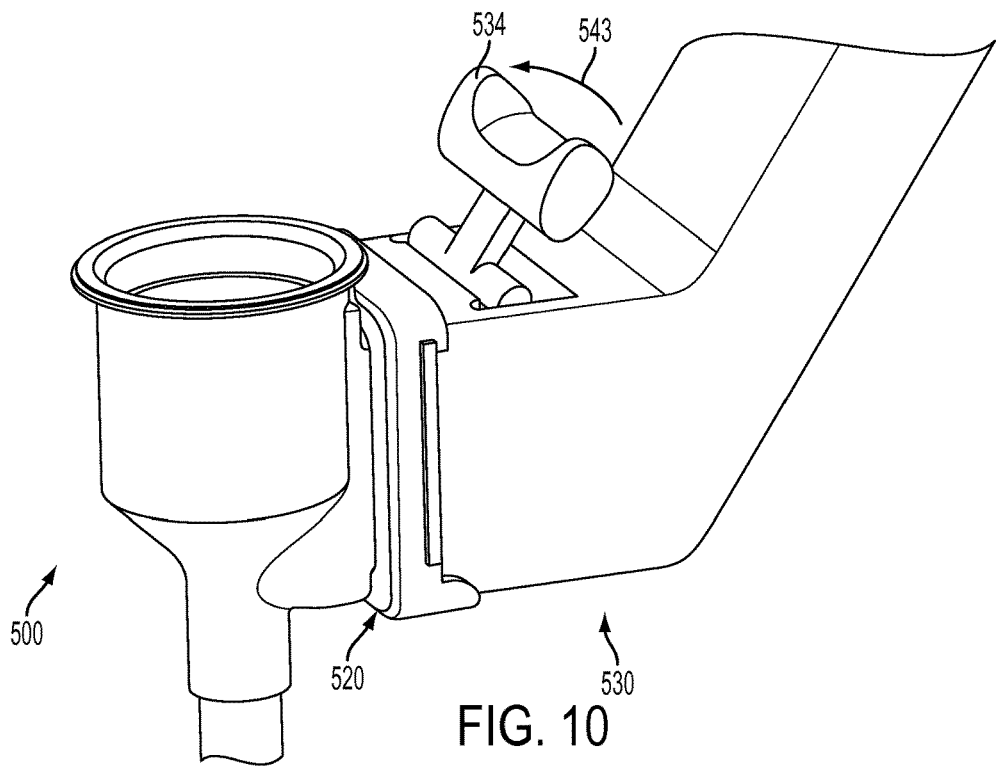
FIG. 10 shows the cannula mount system of FIG. 4 with the handle in a non-depressed position.

The use of cannula mount 530 to mount cannula 500 will now be described with reference to FIGS. 8-11. Turning to FIG. 8, the exemplary embodiment of FIGS. 5, 7, and 8 is shown with handle 534 being depressed along direction 537 to actuate the latching assembly of cannula mount 530. As shown in FIG. 9, actuating handle 534 causes moveable block 554 to be retracted along direction 539, as described above with reference to FIG. 7. When moveable block 554 is retracted along direction 539, spring 560 is compressed and cam surface 556 of moveable block 554 disengages from cam follower surfaces 553 of clamping arms 550. Because spring 560 is no longer biasing cam surface 556 of moveable block 554 into engagement with cam follower surfaces 553, clamping arms 550 are free to pivot to the open position shown in FIG. 9. In the open position shown in FIG. 9, tips 551 of clamping arms 550 are not engaged with cannula sterile adaptor 520, such as, for example, depressions 527 or 1327 of cannula sterile adaptor 520.

With clamping arms 550 in the open position shown in FIG. 9, attachment portion 510 of cannula 500 may be inserted into aperture 522 of cannula sterile adaptor 520, which is already mounted to cannula mount 530. Because cannula 500 may already be inserted into a patient's body, the following movements described for mounting cannula 500 to cannula mount 530, including inserting attachment portion 510 into cannula sterile adaptor 520, may be accomplished by moving the manipulator arm that includes cannula mount 530 relative to a substantially stationary cannula 500. For example, attachment portion 510 may be inserted into cannula sterile adaptor 520 by moving the manipulator arm including cannula mount 530 along direction 538 shown in FIG. 9.

When inserting attachment portion 510 into aperture 522 of cannula sterile adaptor 520, movement of cannula 500 may be constrained. As shown in the exemplary embodiment of FIG. 26, a cannula 1100 may be inserted in a body wall 1140 of a patient. Cannula 1100, cannula sterile adaptor 1120, and cannula mount 1130 may each be arranged according to the exemplary embodiment of FIGS. 5 and 7-11. The insertion of cannula 1100 in body wall 1140 results in constraining movement of cannula 1100 to only pivot about remote center of motion 1142, such as in directions 1144 in FIG. 26. To accommodate the pivoting motion when mounting cannula 1100 to cannula sterile adaptor 1120 and cannula mount 1130, the geometry of a proximal surface 1111 and a distal surface 1113 of cannula attachment portion 1110 may be optimized. The geometry of an inner surface 1121 of cannula sterile adaptor may also be optimized. According to an exemplary embodiment, surfaces 1111, 1113 and 1121 may be curved, such as, for example, at a radius of curvature smaller than a distance from surfaces 1111 and 1121 to remote center 1142. Surfaces 1111, 1113 and 1121 may have other shapes than a curved shape, such as, for example, straight, linear shapes. According to an exemplary embodiment, surfaces 1111, 1113, and 1121 provide two pairs of generally oppositely disposed tapering surfaces, the surfaces of each pair facing away from each other. By shaping surfaces 1111, 1113 and 1121 in this way, insertion and withdrawal of attachment portion 1110 into and out of aperture 1122 of cannula sterile adaptor 1120 is facilitated.

Figure 27:
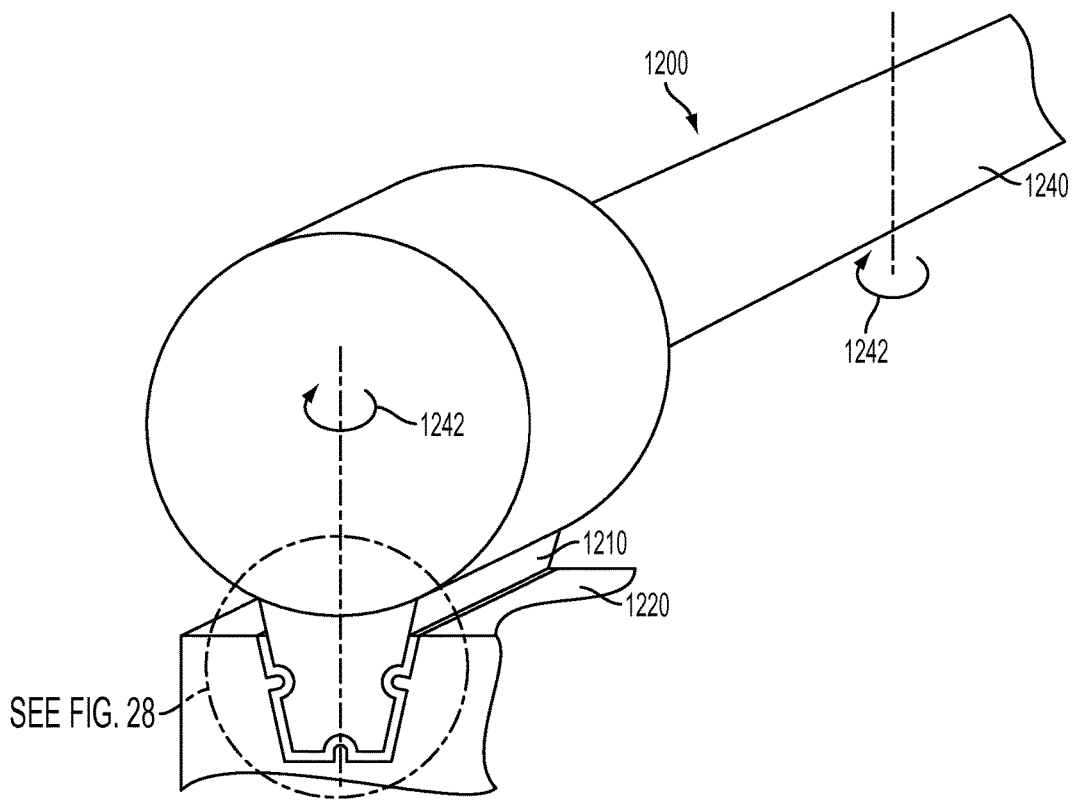
FIG. 27 is a partial perspective view of a cannula mounted to a cannula sterile adaptor, according to another exemplary embodiment.
Figure 28:
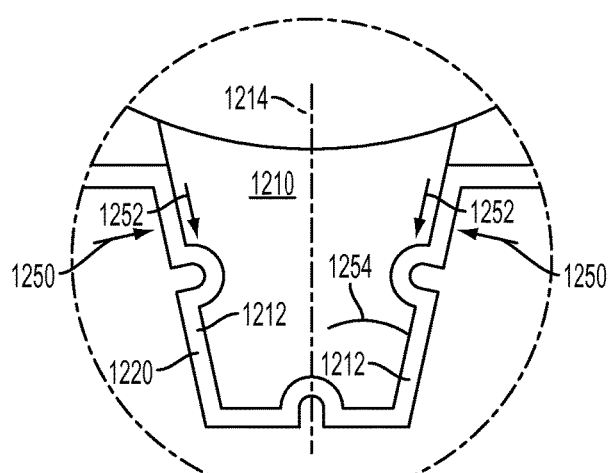
FIG. 28 is an enlarged view of area 28 of FIG. 27.

The geometry of a cannula attachment portion may also be configured in view of forces applied to the cannula. Turning to FIG. 27, an exemplary embodiment of a cannula 1200 is shown in a mounted state with a cannula sterile adaptor 1220. A force 1240, such as, for example, a body wall force, may be applied to cannula, resulting in a torque 1242 upon cannula 1200. Turning to FIG. 28, which is an enlarged view of area of FIG. 27, attachment portion 1210 may be configured to resist the torque and minimize or prevent removal of cannula 1200 from cannula sterile adaptor 1220. As shown in the exemplary embodiment of FIG. 28, side walls 1212 of attachment portion 1210 may be tapered so that a normal force 1250, applied between side walls 1212 and cannula sterile adaptor 1220 to resist torque 1242, has a friction force component 1252 that is sufficient to minimize or prevent torque 1242 from removing attachment portion 1210 from cannula sterile adaptor 1220.

According to an exemplary embodiment, a cross-section of attachment portion 1210 may be tapered, such as along a radial direction with respect to a longitudinal axis of cannula 1200, as depicted in FIGS. 27 and 28, to provide attachment portion 1210 with a wedge shape. For example, side wall 1212 may taper at an angle 1254 relative to a longitudinal centerline 1214 of attachment portion 1210. Angle 1254 may range from, for example, about 8 degrees to about 12 degrees, according to an exemplary embodiment. According to an exemplary embodiment, multiple surfaces of attachment portion 1210 may taper. As depicted in FIG. 26, surfaces 1111 and 1113 may taper. Each of surfaces 1111 and 1113 may be substantially perpendicular to side walls 1212, according to an exemplary embodiment. Thus, attachment portion 1210 may taper on four sides. According to an exemplary embodiment, the side walls of attachment portion 1210 provide attachment portion with a generally square frustum shape. The taper of side walls 1212 and surfaces 1111, 1113 may facilitate removal of attachment portion 1210 from cannula sterile adaptor 1220 when a user actuates a cannula mount (not shown) to release cannula 1200. For instance, the taper can facilitate sliding attachment portion 1210 out of cannula sterile adaptor 1220.

Turning back to FIG. 9, attachment portion 510 may have a shape corresponding to the shape of aperture 522, so that attachment portion 510 may only fit into aperture 522 and an interior 529 of cannula sterile adaptor 520 in a particular orientation, according to an exemplary embodiment. Thus, the proper alignment of attachment portion 510 within aperture 522 is facilitated during mounting of cannula 500 and a user installing cannula 500 will understand that cannula 500 is properly oriented and aligned for mounting once attachment portion 510 has been received within aperture 522. According to an exemplary embodiment, once the attachment portion 510 has been received within aperture 522, cannula 500 may move in only one degree of freedom relative to cannula mount 530, such as to pivot around a line that is perpendicular to the plane of cross-section in FIG. 7. A user may use this behavior to reach the final latching position more easily, because at this point there is only one remaining degree of freedom to reach the latching position. For instance, the remaining degree of freedom is a rotational degree of freedom about the line that is perpendicular to the plane of cross-section in FIG. 7. Once cannula 500 has been maneuvered by pivoting attachment portion 510 into aperture 522, a user can fine tune the position of the attachment portion 510 within aperture along a direction of insertion into aperture 522 (such as by moving a manipulator arm mount 530 is connected to) until a final alignment between attachment portion 510 and cannula sterile adaptor 520 is achieved. Accomplishing the final alignment is facilitated because the cannula is constrained in all other degrees of freedom, thus if the user guides the manipulator arm in the approximate correct direction, the assembly may come into better alignment.

Figure 11:
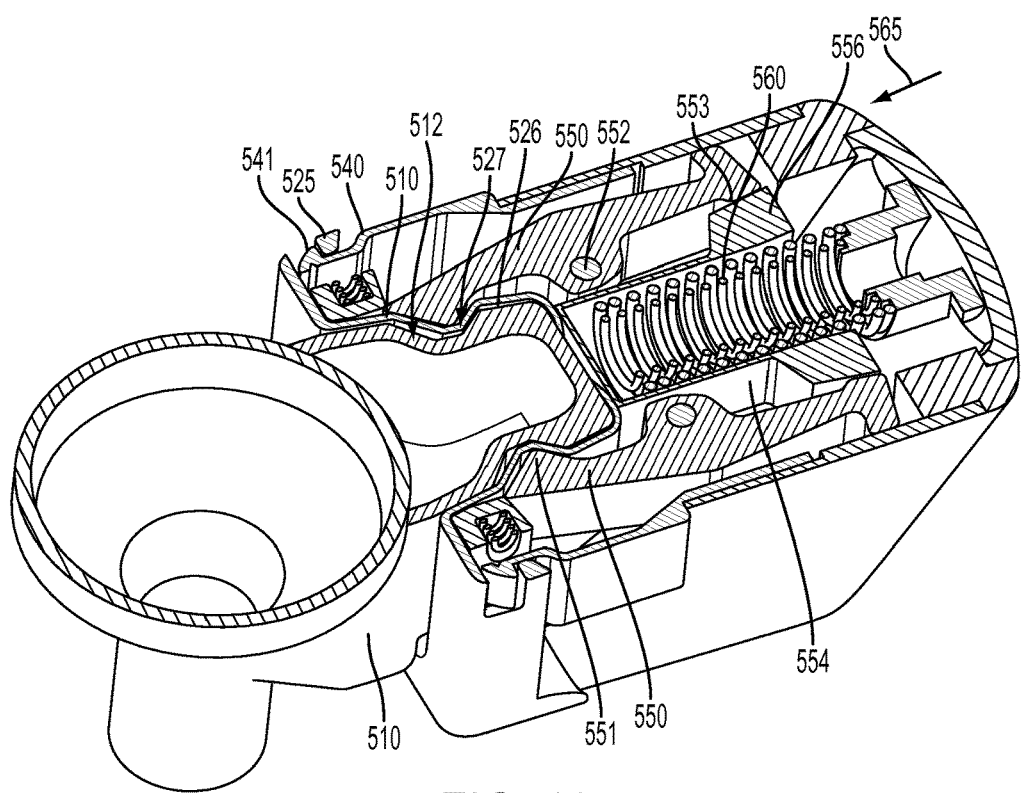
FIG. 11 shows the cannula mount system of FIG. 4 with clamping arms in a closed position and the cannula fully inserted.

As attachment portion 510 is inserted into cannula sterile adaptor 520 in FIG. 9, attachment portion 510 may engage second portion 526 of cannula sterile adaptor 520. However, because second portion 526 may be made of a compliant material, attachment portion 510 may deform second portion 526 to spread apart and permit attachment portion 510 to be easily and fully inserted into interior 529 of cannula sterile adaptor 520. Once attachment portion 510 has been fully inserted into interior 529 of cannula sterile adaptor 520, protrusions 590 of cannula sterile adaptor 520 (or depressions 1327 of cannula sterile adaptor 1320 of FIG. 29) may nest with depressions 512 of attachment portion 510, as shown in FIG. 11. According to an exemplary embodiment, while cannula 500 is being inserted into cannula sterile adaptor 520 and cannula mount 530, handle 534 may remain in the fully depressed position shown in FIG. 8 without requiring a user to hold handle 534 down, due to tips 551 of clamping arms 550 and protrusions 590 of cannula sterile adaptor 520 being unable to enter depressions 512 in attachment portion 510. Thus, a user may be free to focus on properly aligning cannula 500 with cannula sterile adaptor 520 and cannula mount 530 to insert attachment portion 510 within cannula sterile adaptor 520 and cannula mount 530.

Once alignment between attachment portion 510 and cannula sterile adaptor 520 has been accomplished and attachment portion 510 has been fully inserted within cannula sterile adaptor 520, such as in the example of FIG. 11, handle 534 may be released. A force applied by spring 560 biases handle 534 along direction 543 once handle begins to move. When handle 534 is moved along direction 543 in FIG. 11, moveable block 554 (which can be connected to handle 534 via link 535, as shown in FIG. 7) moves along direction 565 shown in FIG. 11. As a result, spring 560 is no longer constrained and is free to bias moveable block 554 along direction 565. As moveable block 554 moves along direction 565, cam surface 556 of moveable block 554 engages cam follower surfaces 553 of clamping arms 550, forcing clamping arms 550 into the closed position shown in FIG. 11 and locking clamping arms 550 in place (e.g., in a closed position). According to an exemplary embodiment, clamping arms 550 and moveable block 554 are not directly connected or directly coupled to one another but instead may engage one another to provide a clamping force to mount a cannula, as discussed above. According to another exemplary embodiment, should lever 534 be released before attachment portion 510 has been fully inserted within cannula sterile adaptor 520, tips 551 of levers 550 may be able to engage depressions 527 of cannula sterile adaptor 520, and protrusions 590 with depressions 512 of attachment portion 510, to draw cannula 500 into cannula mount 530 to complete full insertion of cannula 500 into cannula sterile adaptor 520 and cannula mount 530.

According to an exemplary embodiment, clamping arms 550 and moveable block 554 may be structured to clamp and mount cannulas over a range of motion of clamping arms 550 and block 554. As a result, clamping arms 550 and moveable block 554 provide a large amount of flexibility in accommodating cannulas of different sizes. For instance, a cannula manufacturing process may inherently produce cannulas that vary in size, such as within various manufacturing tolerances. If clamping arms 550 were actuated to close by moving a fixed, predetermined distance, such as by moving a fixed distance until a portion of the clamping arm engages a stop or a mechanism actuating the clamping arm engages a stop, the amount of force clamping arms 550 applied to a cannula would vary upon the size of the cannula. Thus, if a cannula size were on the high side of the manufacturing tolerance, the clamping arms might apply a relatively high clamping force, and if a cannula size were on the low side of the manufacturing tolerance, the clamping arms might apply a relatively low clamping force. The former scenario could result in damage to the cannula and/or mounting device, while the latter scenario could result in the cannula becoming loose within the grip of the clamping arms.

Turning back to FIG. 11, moveable block 554 may engage clamping arms 550 (e.g., via engaging cam follower surfaces 553 of clamping arms 550, as described above) when moveable block 554 is moved, such as along direction 565 due to the force applied by spring 560. As moveable block 554 forces clamping arms 550 to pivot about pins 552, clamping arms 550 may engage a cannula, such as attachment portion 510, as described above, and apply a clamping force to mount the cannula to cannula mount 530. If the cannula has a size on a high side of a manufacturing tolerance, the clamping arms 550 may pivot a smaller distance before engaging the cannula, in comparison to a situation in which a cannula has a size on a low side of a manufacturing tolerance. In either case, moveable block 554 applies a force to clamping arms 550 (e.g., via cam surface 556 and cam follower surfaces 553) to place clamping arms 550 in a closed position, engage a cannula, and apply a clamping force to mount the cannula, whether the clamping arms 550 pivot a relatively smaller distance or a relatively larger distance. Thus, clamping arms 550 may engage and clamp a cannula over various distances clamping arms 550 pivot, which permits clamping arms 550 to accommodate cannulas of various sizes and mount each cannula with a strong clamping force, despite variations in cannula size, such as within a manufacturing tolerance.

Further, because clamping arms 550 may engage and clamp a cannula over the range of motion the clamping arms 550 pivot, clamping arms 550 may accommodate forces applied to a cannula and substantially maintain clamping and mounting of the cannula. For instance, a cannula mounted to cannula mount 530 may experience various high forces applied to the cannula, such as when cannula 500 is bumped or a bodywall force is transmitted to cannula 500 when mounted to cannula mount 530. If clamping arms 550 clamped and mounted the cannula by moving a fixed, predetermined distance, the force could loosen the grip clamping arms 550 had upon the cannula and clamping arms 550 would not adjust to re-establish a clamp force upon the cannula. However, because clamping arms 550 may engage and clamp a cannula over various distances, once the force applied to the cannula has subsided, the clamping force of clamping arms 550 (e.g., the force applied to clamping arms 550 via moveable block 554 and spring 560) cause clamping arms 550 to re-apply a clamping force to the cannula.

When clamping arms 550 are in the closed position, tips 551 of clamping arms 550 may engage depressions 512 of attachment portion 510 to securely latch cannula 500 to cannula mount 530. The biasing force of spring 560 on moveable block 554, for example, may provide a strong clamping force of clamping arms 550 on attachment portion 510 (as well as cannula sterile adaptor 520 when adaptor 520 also has been mounted, as shown in FIG. 11) when clamping arms 550 are in the closed position. As a result, cannula 500 may be securely mounted to cannula mount 530 and resist releasing under a load, such as when cannula 500 is subjected to a body wall force while inserted into a patient during a surgical procedure. Further, the latching assembly of cannula mount 530 (e.g., clamping arms 550, moveable block 554, and spring 560) facilitates a user to easily determine when cannula has been properly aligned and latched, which can minimize or prevent a user from trying to physically force cannula 500 into cannula mount 530, which in turn could damage cannula 500 and/or cannula mount 530.

Figure 12:
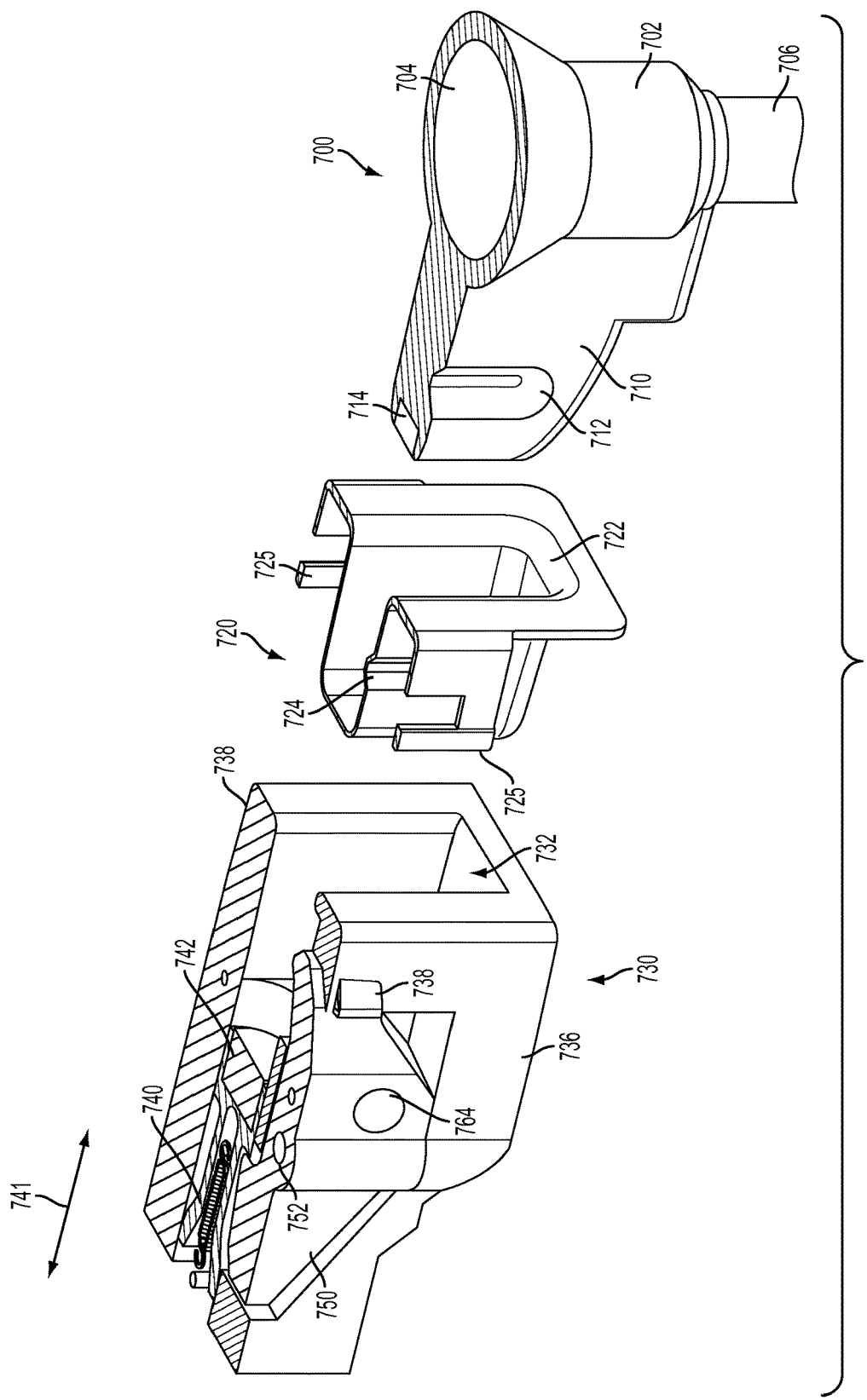
FIG. 12 is an exploded view of a cannula mount system with interior portions depicted, according to another exemplary embodiment.

The various embodiments of this disclosure are not limited to the exemplary embodiments described above in regard to FIGS. 5-11 and may instead include various other arrangements for mounting a cannula to a cannula mount of a manipulator arm of a patient side cart. Turning to FIG. 12, a cannula 700, cannula sterile adaptor 720, and cannula mount 730 of a patient side cart are shown, according to another exemplary embodiment. Cannula mount 730 may be, for example, cannula mount 124 provided on one of manipulator arms 110-113 of patient side cart 100 of FIG. 1. Cannula 700 may include a bowl section 702, proximal end 704, tube 706, and attachment portion 710, similar to cannula 300 in the exemplary embodiment of FIG. 2. According to an exemplary embodiment, attachment portion 710 may include a depression 712 to assist with mounting cannula 700 to cannula mount 730, as will be discussed below. Attachment portion 710 may include a single depression 712, such as on one side of attachment portion 710, as shown in the exemplary embodiment of FIG. 12, although attachment portion 710 is not limited to a single depression 712 and instead include a plurality of depressions 712, such as when cannula mount 730 includes a plurality of clamping arms 750, which will be discussed below. According to an exemplary embodiment, attachment portion 710 may include a metal member 714 to facilitate mounting of cannula 700 to cannula mount 730, as will be discussed below. Metal member 714 may be, for example, a ferrous metal member. According to an exemplary embodiment, metal member 714 may be made of a magnetic steel alloy, such as a magnetic grade of stainless steel (e.g., 17-4 PH stainless steel).

Cannula sterile adaptor 720 may include an aperture 722 sized and shaped to receive attachment portion 710 of cannula 700. As discussed above in regard to the exemplary embodiment of FIG. 3, cannula sterile adaptor 720 may be attached to a surgical drape (not shown in FIG. 12) to facilitate forming a boundary between a sterile region (e.g., where cannula 700 is located) and a non-sterile region (e.g., where cannula mount 730 is located). Although cannula sterile adaptor 720 is depicted in the exemplary embodiment of FIG. 12 as being made of a single piece, cannula sterile adaptor 720 may include different portions with different properties to facilitate mounting of the cannula sterile adaptor 720 and/or cannula 700 to cannula mount 730. For example, cannula sterile adaptor 720 may include a first portion and a second portion, as discussed above with regard to the exemplary embodiment of FIGS. 4, 5, and 7-11.

Cannula sterile adaptor 720 may include structures to mount cannula sterile adaptor 720 to cannula mount 730. According to an exemplary embodiment, cannula sterile adaptor 720 may include one or more retention features 725 to engage with one or more complementary retention features 738 of cannula mount 730 for mounting cannula sterile adaptor 720 to cannula mount 730. As shown in the exemplary embodiment of FIG. 12, cannula sterile adaptor 720 and cannula mount 730 may each include a plurality of retention features, such as a pair of retention features 725 and 738 on respective opposing sides of cannula sterile adaptor 720 and cannula mount 730. Retention features 725 and 738 may be respectively molded as one piece with cannula sterile adaptor 520 and a body 736 of cannula mount 730, according to an exemplary embodiment, or may be provided as separate pieces respectively joined to cannula sterile adaptor 720 and body 736. Retention features 725 and 738 may be configured to disengage with one another, such as via at least one of retention features 725 and 738 moving relative to cannula sterile adaptor 720 or cannula mount 730. According to an exemplary embodiment, retention feature 738 may be arranged to move relative to body 736, such as, for example, against a force applied by a biasing spring, as discussed above with regard to FIG. 5.

Cannula mount 730 may include structures to mount cannula 700 in a secure and reliable manner that is also easy to use. According to an exemplary embodiment, cannula mount 730 may include a moveable block 740 arranged to move within a housing body 736 along directions 741 indicated in FIG. 12. Moveable block 740 may include a magnet 742. Magnet 742, for example, can be a permanent magnet made of an alloy familiar to one of ordinary skill in the art. For example, magnet 742 may be a neodymium magnet or other permanent magnet familiar to one of ordinary skill in the art. Magnet 742 may be used to facilitate mounting of cannula 700 to cannula mount 730, as will be discussed below.

Cannula mount 730 may further include a clamping arm 750 to engage with cannula 700, as well as cannula sterile adaptor 720 when cannula sterile adaptor 720 has been mounted to cannula mount 730. As shown in the exemplary embodiment of FIG. 12, clamping arm 750 may be a single clamping arm to simplify the construction and cost of cannula mount 730, although cannula mount 730 may include a plurality of clamping arms 750, including a second opposing clamping arm having a mirror-image construction of clamping arm 750, instead of the single clamping arm 750 shown in FIG. 12. Clamping arm 750 may be arranged to pivot about pin 752 between an open and closed position, with clamping arm 750 being biased to a closed position by a biasing device.

Figure 13:
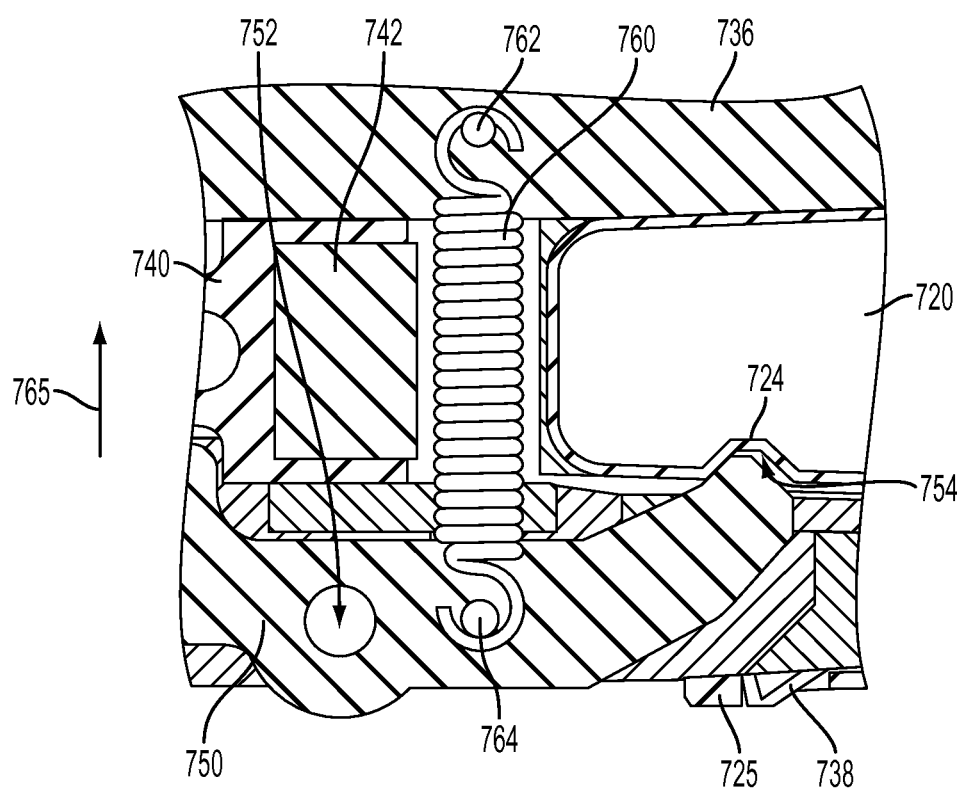
FIG. 13 is a partial interior, plan view of the cannula mount system of FIG. 12.

Turning to FIG. 13, a plan view of a portion of the mount 750 of FIG. 12 is shown to further illustrate internal components of cannula mount 730. In FIG. 13, clamping arm 750 is depicted in a closed position, with tip 754 of clamping arm engaging cannula sterile adaptor 720. According to an exemplary embodiment, tip 754 may be inserted into a depression 724 of cannula sterile adaptor 720 to facilitate mounting of cannula sterile adaptor 720 to cannula mount 730. A biasing device to bias clamping arm 750 to the closed position shown in FIG. 13 may be, for example, a spring 760 or other type of biasing device familiar to one of ordinary skill in the art. Spring 760 may be, for example, a coil spring. Spring 760 may be connected between body 736 of cannula mount 730 and clamping arm 750, such as between a pin 762 connected to body 736 and a pin 764 connected to clamping arm 750. In this way, spring 760 may bias clamping arm 750 to pivot about pin 752 into the closed position shown in FIG. 13. Although spring 760 appears to be located between moveable block 740 and cannula sterile adaptor 720 in FIG. 13, spring 760 may be located, for example, vertically below moveable block 740 into the page of FIG. 13 so spring 760 does not interfere with the function of moveable block 740 to facilitate mounting of cannula 700, as will be discussed below.

Figure 14:
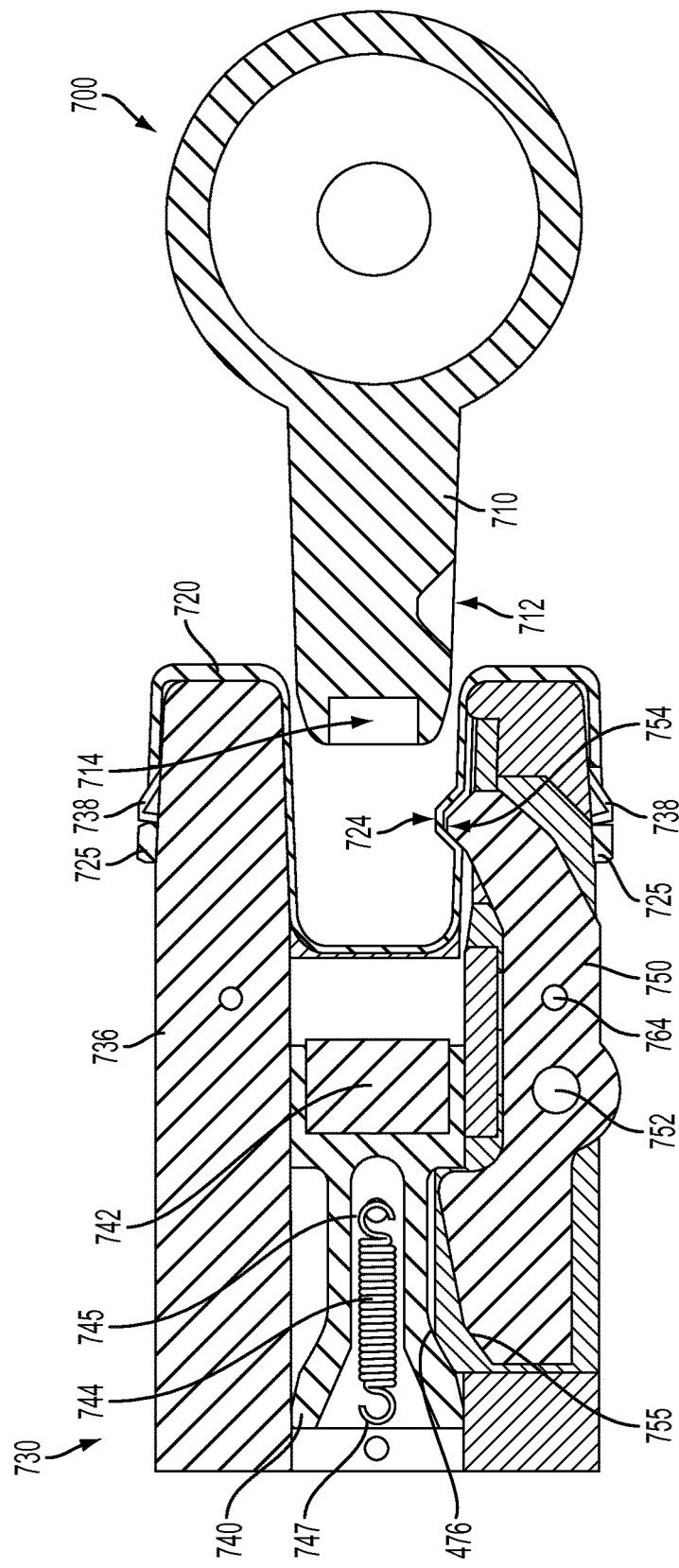
FIG. 14 is a plan partial view, with interior portions depicted, of the cannula mount system of FIG. 12.

The mounting of cannula 700 to cannula mount 730 will now be discussed with reference to FIGS. 14-16. FIG. 14 is a plan view showing cannula sterile adaptor 720 in a mounted state within cannula mount 730, and showing cannula 700 as attachment portion 710 is being inserted into cannula sterile adaptor 720 and cannula mount 730 (e.g., into aperture 722 of cannula sterile adaptor 720 and aperture 732 of cannula mount 730 shown in FIG. 12). Thus, FIG. 14 depicts an initial stage of mounting cannula 700 to cannula mount 730. In the initial mounting stage shown in FIG. 14, clamping arm 750 is biased to a closed position, such as by spring 760, and moveable block 740 is biased to the unlatched position shown in FIG. 14 by a biasing device. Moveable block 740 may be biased to the position shown in FIG. 14 by, for example, a spring 744 or other biasing device connected between moveable block 740 and body 736 of cannula mount 730. For example, a first end 745 of spring 744 may be connected to moveable block 740 and a second end 747 of spring 744 may be connected to body 736. Because moveable block 740 can be biased to the unlatched position shown in FIG. 14, any magnetic attraction between magnet 742 and metal member 714 of attachment portion may be too weak over the distances between magnet 742 and metal member 714 in FIG. 14 to overcome the force applied by the biasing device of moveable block (e.g., spring 744). Thus, moveable block 740 and magnet 742 remain in the unlatched position shown in FIG. 14.

Figure 15:
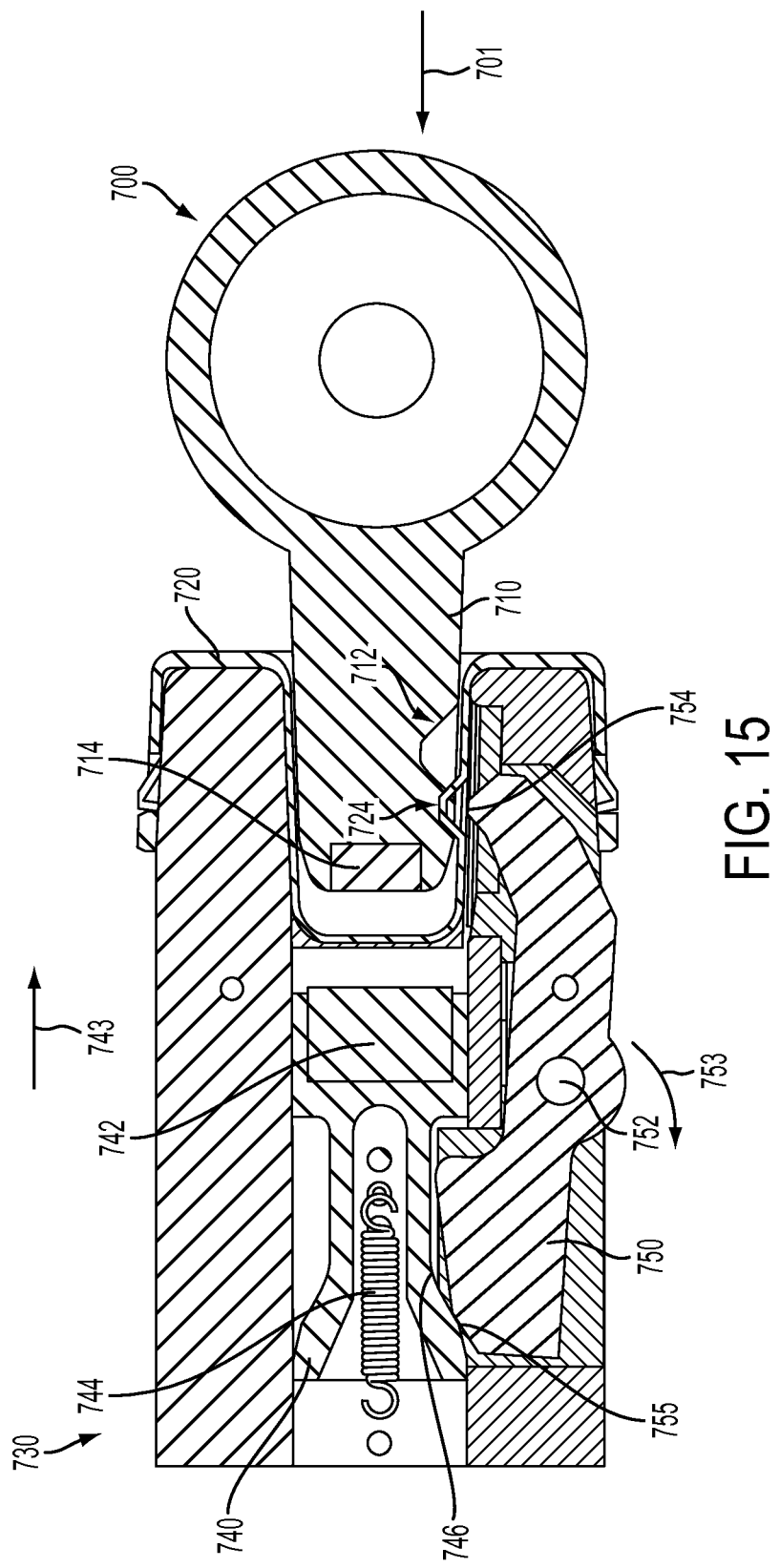
FIG. 15 is a partial plan view, with interior portions depicted, of the cannula mount system of FIG. 12 showing the cannula partially inserted.

Turning to FIG. 15, the cannula 700 of FIG. 14 has been inserted along direction 701 in FIG. 15 so attachment portion 710 is further inserted into cannula sterile adaptor 720 and cannula mount 730. As cannula 700 is inserted along direction 701, attachment portion 710 engages the portion of cannula sterile adaptor 720 forming depression 724. According to an exemplary embodiment, the portion of cannula sterile adaptor 720 forming depression 724 may be flexible (portions of adaptor 720 surrounding depression 724 may be flexible as well), such as, for example, second portion 526 discussed above with regard to the exemplary embodiment of FIGS. 4, 5, and 7-11. Thus, attachment portion 710 may deform the portion of cannula sterile adaptor 720 forming depression 724 as attachment portion 710 is inserted. Further, as attachment portion 710 of cannula 700 is inserted, attachment portion 710 may apply a force to tip 754 of clamping arm 750, such as when portion of cannula sterile adaptor 720 forming depression 724 is deformed, causing clamping arm 750 to be opened from its closed position. For example, clamping arm 750 may pivot about pin 752 in direction 753 to an open position shown in FIG. 15. Thus, a user may open clamping arm 750 simply by inserting attachment portion 710 to force clamping arm 750 open As cannula 700 is inserted to the position shown in FIG. 15, a magnetic attraction force between magnet 742 and metal member 714 increases. When attachment portion 710 and metal member 714 are within close enough proximity to each other, as shown in FIG. 15, the attractive force is strong enough to overcome the biasing force applied to moveable block 740 by the biasing device (e.g., spring 744), causing moveable block 740 and magnet 742 to move forward along direction 743 in FIG. 15. As this occurs, a cam surface 746 of moveable block 740 may engage with a cam surface of clamping arm 750, such as a first cam follower surface 755 of clamping arm 750, causing movement of moveable block 740 and magnet 742 to cease when the cam surface 746 and cam follower surface 755 engage. Thus, clamping arm 750 and attachment member 710 are not latched to one another and cannula 700 is not yet in a mounted state to cannula mount 730.

Figure 16:
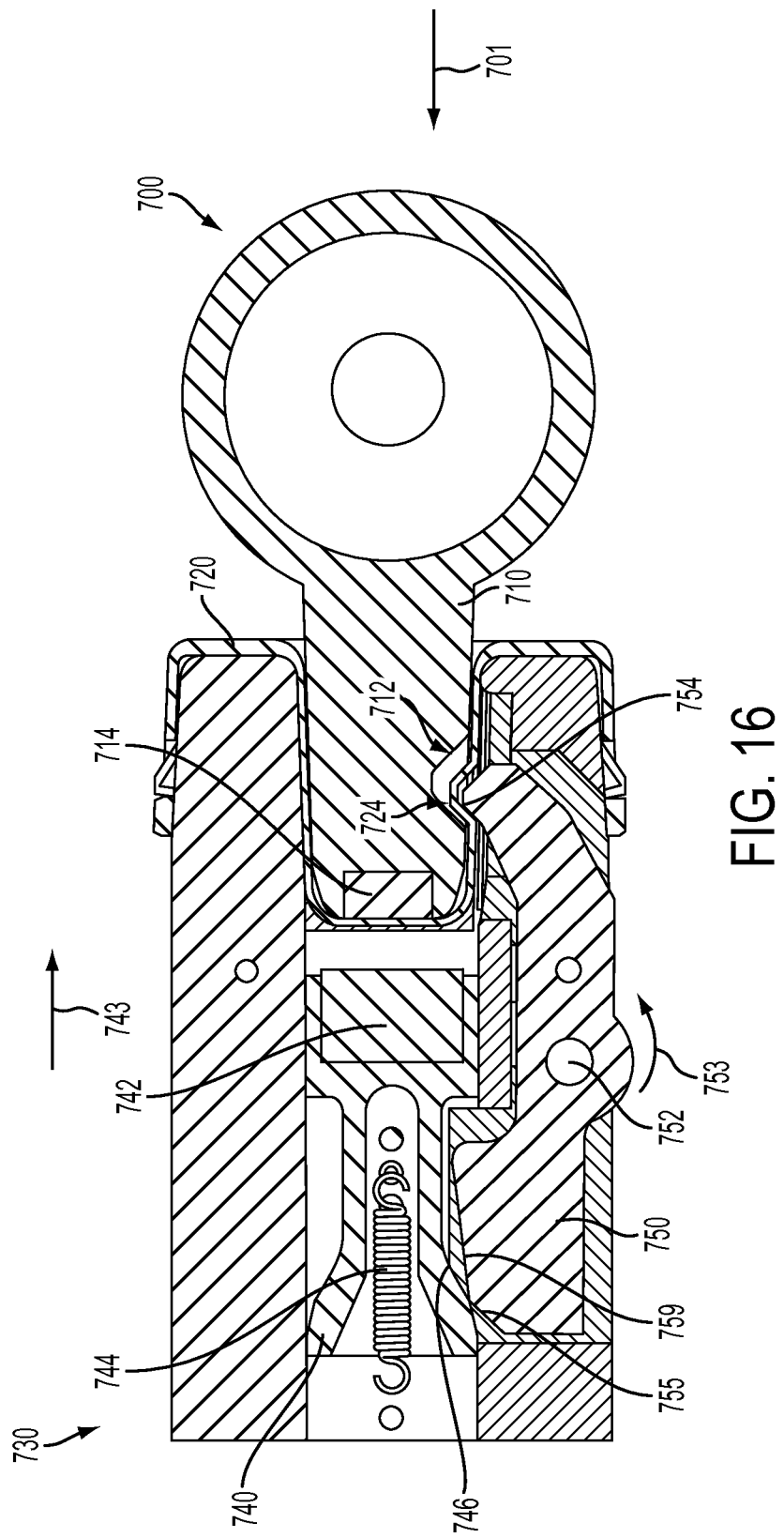
FIG. 16 is a partial plan view of the cannula mount system of FIG. 12 showing the cannula fully inserted.

Turning to FIG. 16, cannula 700 is depicted in a fully inserted position in cannula sterile adaptor 720 and cannula mount 730 along direction 701. In the fully inserted position, the portion of cannula sterile adaptor 720 forming depression 724 may nest within depression 712 of attachment portion 710. When attachment portion 710 has been inserted a sufficient amount along direction 701 to permit tip 754 of clamping arm 750 to enter depression 712 (as well as depression 724 of cannula sterile adaptor 720), clamping arm 750 may be free to pivot about pin 752 along direction 757 in FIG. 16.

Further, as attachment portion 710 approaches the position shown in FIG. 16, the force of the magnetic attraction between magnet 742 and metal member 714 increases even further. According to an exemplary embodiment, when clamping arm 750 pivots along direction 757, moveable block 740 and magnet 742 advance along direction 743 in FIG. 16 until magnet 742 reaches the latched position shown in FIG. 16. Clamping arm 750 and moveable block 740 may be mechanically timed so that clamping arm 750 and moveable bock 740 move at substantially the same time to mount cannula 700 to cannula mount 730. Thus, the pivoting of clamping arm 750 in direction 757 to engage attachment portion 710 and the movement of moveable block 740 and magnet 742 may move at substantially the same time, according to an exemplary embodiment.

When moveable block 740 and magnet 742 reach the latched position shown in FIG. 16, cam surface 746 of moveable block 740 may engage a cam follower surface of clamping arm 750. Although cam surface 746 may engage first cam follower surface 755 of clamping arm 750 to apply a clamping force to cannula 700, clamping arm 750 may include other cam follower surfaces to engage with moveable block 740. For example, when clamping arm 750 pivots along direction 757, cam surface 746 of moveable block 740 may disengage with first cam follower surface 755 and engage a second cam follower surface 759 of clamping arm 750. According to an exemplary embodiment, second cam follower surface 759 may have a smaller slope (e.g., smaller angle relative to cam surface 746) than first cam follower surface 755 so that second cam follower surface 759 engages cam surface 746 of moveable block 740 to a higher degree than first cam follower surface 755, creating a significant latch force between cam follower surfaces 755 and 759 to hold clamping arm 750 in position and securely mount cannula 700 to cannula mount 730. Cam surface 746 may be configured to engage second cam follower surface 759 so a clamping force is provided to clamping arm 750 when tip 754 is positioned to be inserted within depressions 724 and 712, according to an exemplary embodiment. Due to the engagement between cam surfaces of moveable block 740 and clamping arm 750 (e.g. between cam surface 746 and first cam follower surface 755 or second cam follower surface 759), clamping arm 750 may clamp and mount a cannula over a range of movements (e.g., including a maximum travel distance for moveable block 740), which permits clamping arm 750 to accommodate cannulas of various sizes.

According to an exemplary embodiment, in the latched position, moveable block 740 may be engaged with (e.g., in contact with) an object that forms a hard stop to stop movement of moveable block 740, such as, for example, a portion of cannula mount body 736 that forms a hard stop. According to an exemplary embodiment, in the latched position, magnet 742 may be attracted to metal member 714 but prevented from contacting the metal member 714. According to an exemplary embodiment, magnet 742 may be prevented from contacting cannula sterile adaptor 720. For example, tip 754 of clamping arm 750 may engage a cannula (or engage cannula through a cannula sterile adaptor), causing second cam follower surface 759 of clamping arm 750 to engage cam surface 745 of moveable block 740, which may in turn cause moveable block 740 and magnet 742 to stop moving before magnet 742 an object that would otherwise stop movement of block 740 and magnet 742.

To release cannula 700 from cannula mount 730, a user may pull back the cam block 740, thus freeing the clamping arm 750 to pivot about pin 752 to the open position of FIG. 15 and then pull cannula 700 out of cannula mount 730 with a sufficient force to open the levers 750 to allow the cannula to be removed. According to an exemplary embodiment, cannula mount 730 may further include a release mechanism (not shown) to force moveable member 740 in a direction opposite to direction 743 in FIG. 15 to force magnet 742 and metal member 714 apart and facilitate removal of cannula 700 from cannula mount 730. For example, a release mechanism may be a member that is depressed downward between magnet 742 and metal member 714 to force moveable block 740 in a direction opposite to direction 743 in FIG. 16 until the magnetic attraction between magnet 742 and metal member 714 is overcome, permitting spring 744 to bias moveable block 740 to the position shown in FIG. 14.

According to an exemplary embodiment, magnet 742 may be selected to provide a magnetic force to facilitate insertion of cannula 700 within cannula mount 730 once attachment portion 710 has been inserted a sufficient distance. For example, once attachment portion 710 has been inserted to the position shown in FIG. 15, or a position between the positions of FIG. 15 and FIG. 16, the attractive magnetic force between magnet 742 and metal member 714 may be sufficient by itself to draw attachment portion 710 further into cannula mount 730 and to the position shown in FIG. 16, permitting clamping arm 750 and magnet 742 to latch to attachment portion 710 and mount cannula 700 to cannula mount 730. As a result, a final stage of inserting cannula 700 into cannula mount 730 and latching cannula 700 to cannula mount 730 may be made substantially automatic once cannula 700 has been inserted a sufficient distance for magnet 742 to draw cannula 700 into cannula mount 730, resulting in arm 750 clamping cannula 700 (e.g., due to a force applied by moveable block 740, via cam surface 746 and cam follower surface 755 or 759).

Features of the exemplary embodiment of FIGS. 12-16 may be used in combination with the features of various embodiments described herein. For example, the exemplary embodiment of FIGS. 4, 5, and 7-11 may include magnet (e.g., magnet 742), such as, for example, in moveable block 554. Further, the exemplary embodiment of FIGS. 12-16 may be used in combination with the features of various embodiments described herein. For example, cannula mount 730 may include two clamping arms instead of a single clamping arm 750.

Figure 17:
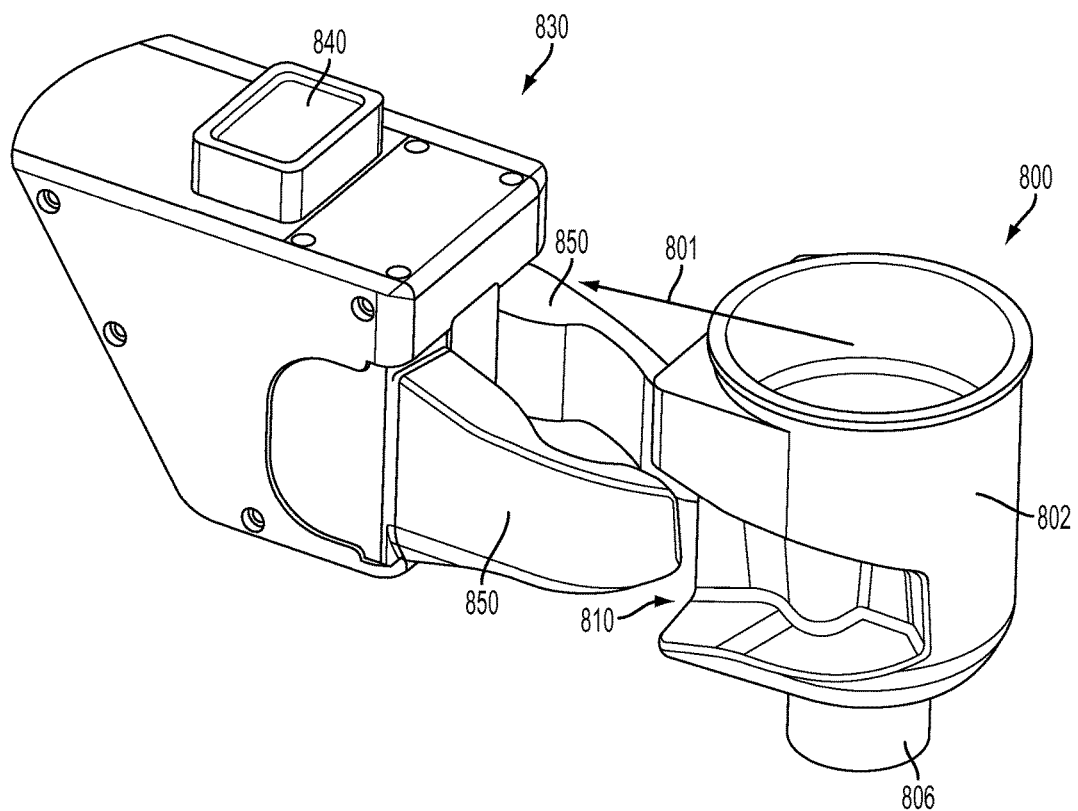
FIG. 17 is an exploded perspective view of a cannula mount system, according to yet another exemplary embodiment.
Figure 18:
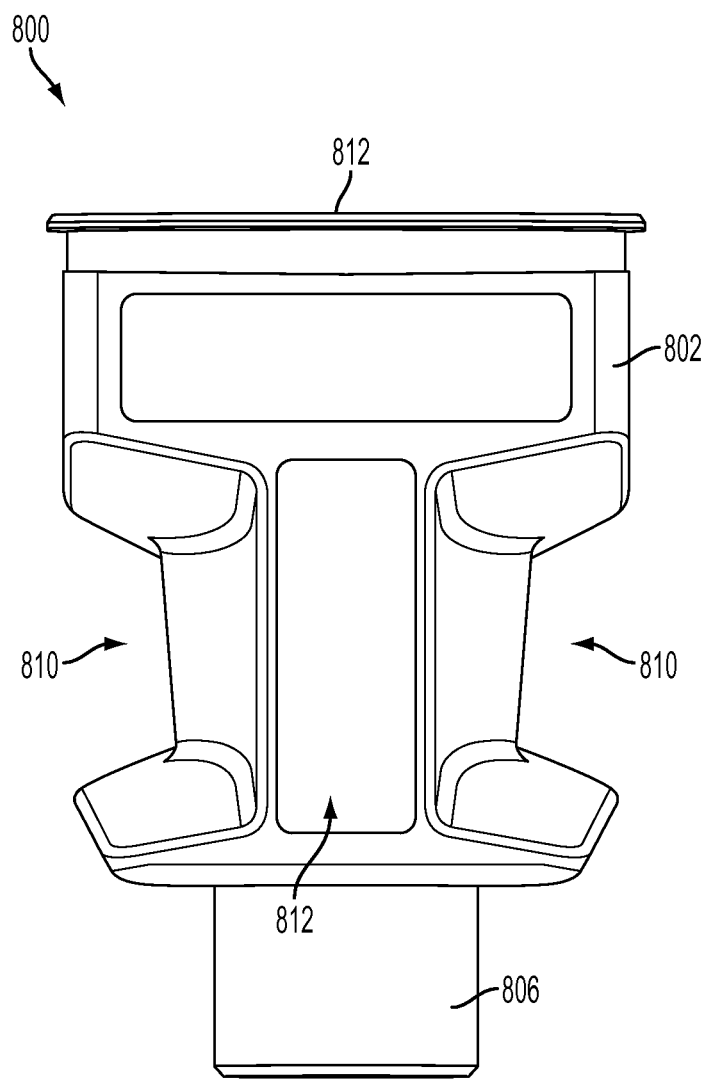
FIG. 18 is a side view of a cannula, according to an exemplary embodiment.

Turning to FIG. 17, another exemplary embodiment of a system for mounting a cannula to a cannula mount of a manipulator arm of a patient side cart is depicted. In the exemplary embodiment of FIG. 17, a cannula 800 may be mounted to a cannula mount 830 by inserting cannula 800 along direction 801 between clamping arms 850 of cannula mount 830. Cannula mount 830 may be, for example, cannula mount 124 provided on one of manipulator arms 110-113 of patient side cart 100 of FIG. 1. Cannula 800 may include a bowl section 802 and a tube 806. Further, as shown in FIGS. 17 and 18, cannula 800 may include depressions 810 to receive clamping arms 850. Depressions 810 may have shapes corresponding to the shapes of clamping arms 850 to facilitate depressions 810 receiving clamping arms 850 when clamping arms 850 clamp cannula 800 to mount cannula 800 to cannula mount 830. Thus, clamping arms 850 may mount cannula 800 without cannula mount 830 (or a cannula sterile adaptor, not shown) including an aperture to receive a portion of cannula 800 inserted into cannula mount 830 (or inserted into the cannula sterile adaptor). Cannula 800 may further include a metal member 812, as shown in FIG. 18.

Although the exemplary embodiment of FIG. 17 does not depict a cannula sterile adaptor (which has been omitted for ease of viewing), the exemplary embodiment of FIG. 17 may include a cannula sterile adaptor, which may be positioned between cannula 800 and cannula mount 830. As discussed above in regard to the exemplary embodiment of FIG. 3, the cannula sterile adaptor may be attached to a surgical drape (not shown in FIG. 17) to facilitate forming a boundary between a sterile region (e.g., where cannula 800 is located) and a non-sterile region (e.g., where cannula mount 830 is located). Further the cannula sterile adaptor may be made of a single piece or different parts with different properties, as discussed above with regard to the exemplary embodiment of FIGS. 4, 5, and 7-11.

Figure 19:
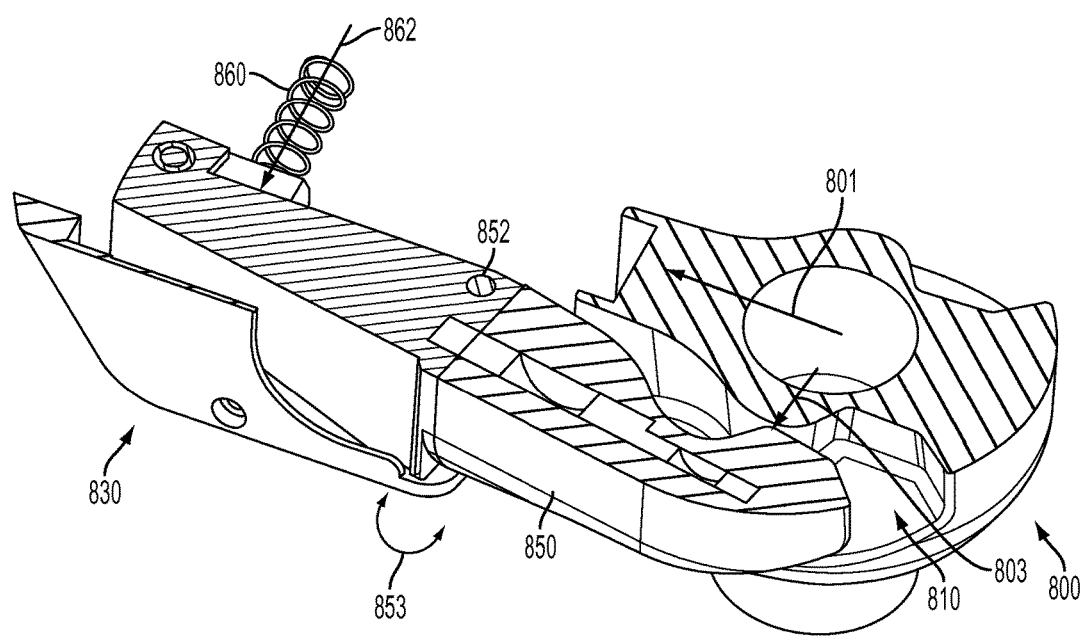
FIG. 19 is a partial perspective view of the cannula and cannula mount, with interior portions depicted, of the exemplary embodiment of FIG. 17.

Cannula mount 830 may include a device to bias clamping arms 850 to a predetermined position. Turning to FIG. 19, which depicts cannula 800 and cannula mount 830 with an interior of cannula mount 830 partially exposed and only one clamping arm 850 shown for ease of illustration, cannula mount 830 may include a spring 860 or other biasing device. Each clamping arm 850 may be structured to pivot about a pin 852, such as in directions 853. Spring 860 may be connected to clamping arm 850 to apply a force along direction 862 to pivot clamping arm 850 along directions 853 to a closed position in which clamping arms 850 may apply a clamping force and mount cannula 800 to cannula mount 830. As shown in FIG. 19, cannula 800 may be mounted to cannula mount 830 by inserting cannula 800 into cannula mount 830 along direction 801 between clamping arms 850 (e.g., by moving a manipulator arm including cannula mount 830 so cannula 800 is inserted into cannula mount 830), causing clamping arm 850 to be opened (causing the pair of clamping arms, not shown in FIG. 19, to be forced apart) along direction 803 (e.g., by pivoting clamping arm 850 about pin 852) against the force applied by spring 860. In another example, clamping arms 850 of cannula mount 830 may be opened by depressing a release button 840, which will be described in further detail below, to permit insertion of cannula 800 along direction 801.

Figure 20:
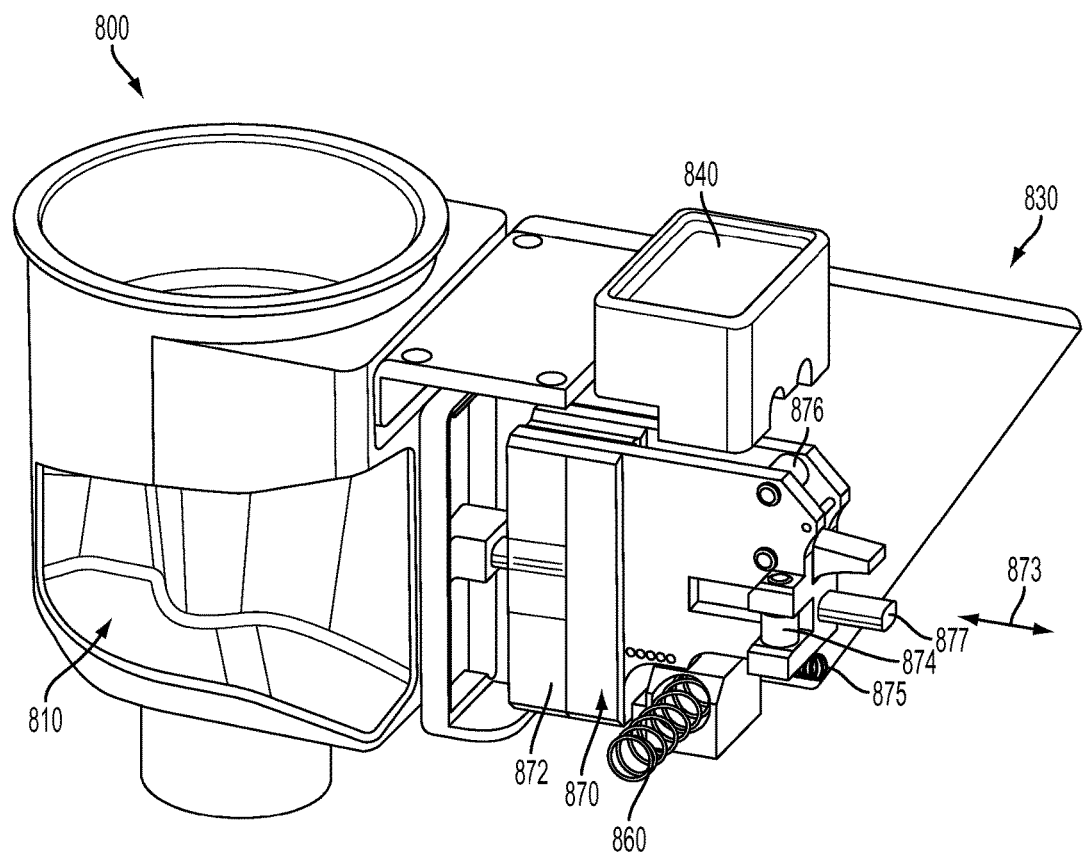
FIG. 20 is another partial perspective view of the cannula mount and cannula, with interior portions depicted, of the exemplary embodiment of FIG. 17.

As described above, cannula 800 may include a metal member 812. According to an exemplary embodiment, cannula mount 830 may include a magnet that is attracted to metal member 812. Thus, when cannula 800 is inserted a sufficient distance between clamping arms 850, the magnet may attract the metal member 812, which may assist in drawing cannula 800 along direction 801 to a fully mounted position. The magnet may be located on a moveable member within cannula mount 830 to permit the magnet to move toward the metal member 812 of cannula 800 as well. Turning to FIG. 20, cannula 800 and cannula mount 830 are shown, with internal features of cannula mount 830 partially shown for ease of viewing. As shown in FIG. 20, cannula mount 830 may include a moveable block 870. According to an exemplary embodiment, moveable block 870 may slide along a shaft 877, such as along direction 873 in FIG. 20. Moveable block 870 may be biased to a position away from cannula 800, such as by a spring 875 or other biasing device, until cannula 800 has been inserted a sufficient distance to cause the magnetic force between metal member 812 of cannula 800 and a magnet located within moveable block 870 to overcome the biasing force of spring 875, causing moveable block 870 to slide along shaft 877 toward cannula 800.

Figure 21:
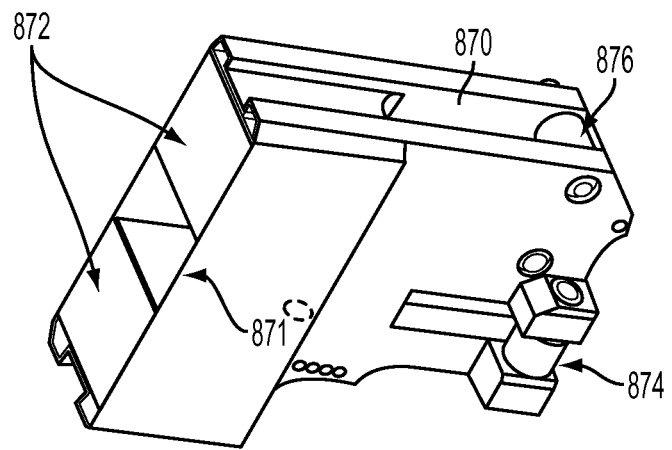
FIG. 21 is a perspective view of a moveable block, as used in the cannula mount system of FIG. 17, according to an exemplary embodiment.
Figure 23:
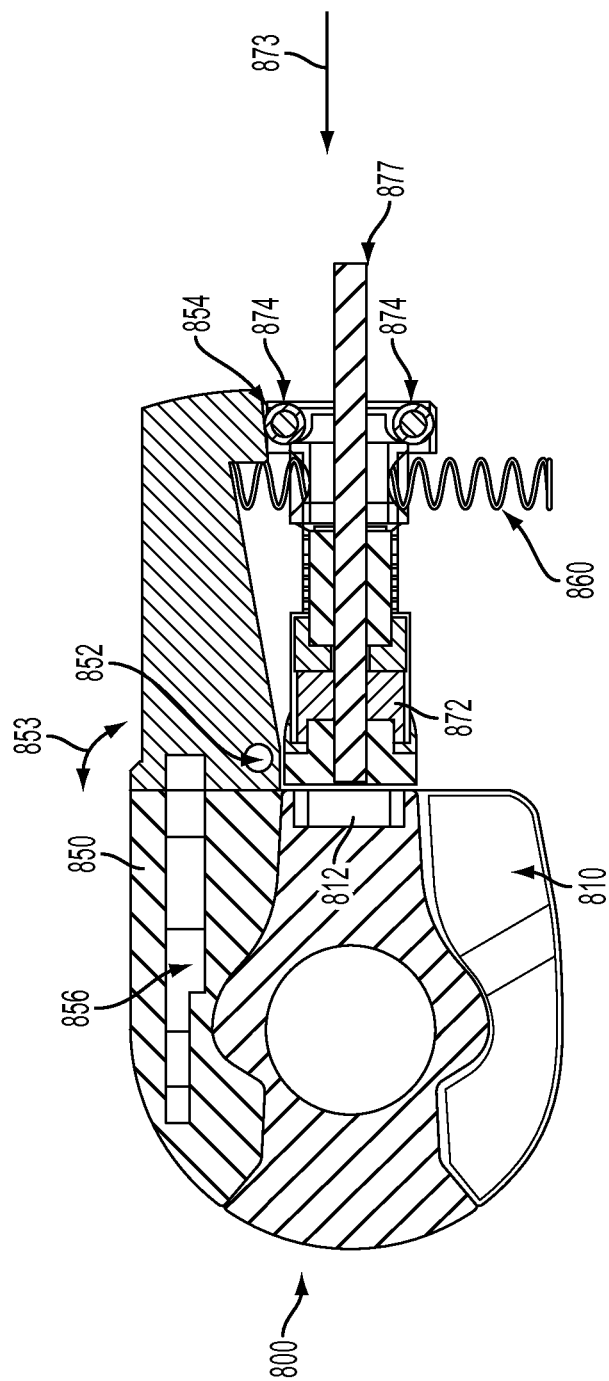
FIG. 23 is a partial plan view, with interior portions depicted, of a cannula in a mounted position with the cannula mount of FIG. 17.

Moveable block 870 may include structures to actuate clamping arms 850 as moveable block 870 moves and engages clamping arms 850. Turning to FIG. 21, a perspective view of moveable block 870 is shown, which may include a magnet and an aperture 871 through which shaft 877 may extend. According to an exemplary embodiment, the magnet may be a horseshoe magnet 872, the ends of which are shown in FIG. 21. Moveable block 870 may further include a clamping arm engaging surface 874 for each clamping arm (e.g., on opposite sides of moveable block 870, as shown in FIG. 23, when cannula mount 830 includes a pair of clamping arms 850) and a release engaging surface 876. The partial exposed view of FIG. 20 depicts interior features of an exemplary embodiment of moveable block 870, including magnet 872, as well as a clamping arm engaging surface 874 and a release engaging surface 876. Clamping arm engaging surfaces 874 and release engaging surface 876 may be, for example, rollers, cam surfaces, or other types of engaging surfaces familiar to one of ordinary skill in the art.

Figure 22:
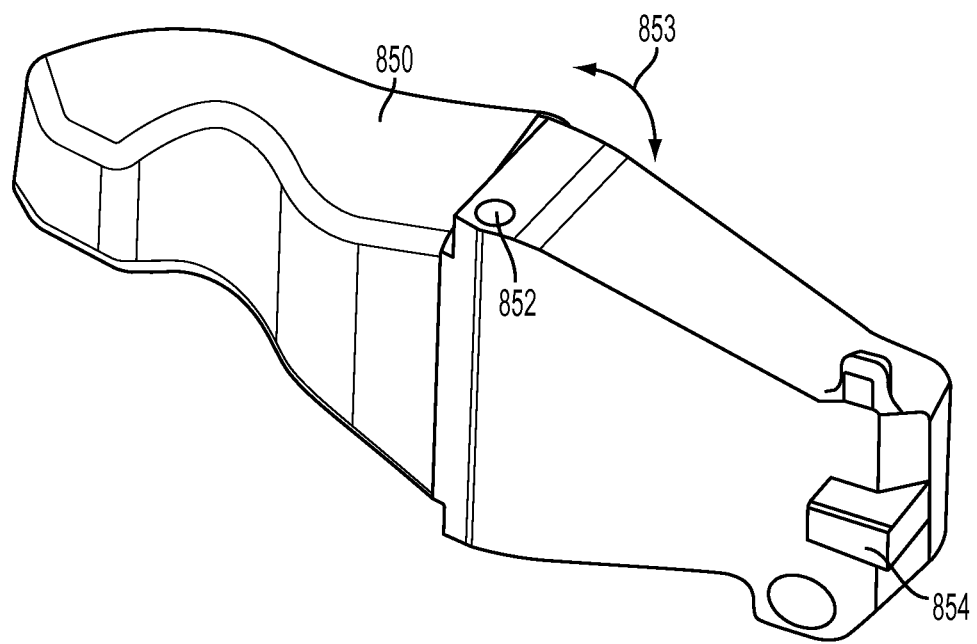
FIG. 22 is a perspective view of a clamping arm, as used in the cannula mount system of FIG. 17, according to an exemplary embodiment.

Clamping arms 850 may include structures to engage with moveable block 870 as moveable block 870 moves so that clamping arms 850 may be actuated by moveable block 870. Turning to FIG. 22, a perspective view is shown of a clamping arm 850 for cannula mount 830, with clamping arm 850 including a cam follower surface 854 to engage with moveable block 870. For example, when moveable block 870 moves along direction 873 in FIG. 23 toward cannula 800, such as due to the magnetic attraction between metal member 812 of cannula 800 and magnet 872 of moveable member 870, a clamping arm engaging surface 874 of moveable block 870 may engage cam follower surface 854. When clamping arm engaging surface 874 is a roller, the roller may roll along and press against cam follower surface 854 as moveable block 870 moves toward cannula 800, although clamping arm engaging surface 874 may also be a cam surface that slides against cam follower surface 854 of clamping arm 850. Although a single clamping arm 850 is shown in FIG. 23, moveable block 870 may actuate a plurality of clamping arms, such as the pair of clamping arms 850 shown in FIG. 17, which may be positioned on opposite sides of moveable block 870.

As clamping arm engaging surface 874 presses against cam follower surface 854, clamping arm 850 is actuated to pivot about pin 852, such as in direction 853 in FIG. 23, to close clamping arm 850 upon cannula 800 (e.g., by receiving clamping arm 850 within depression 810) so that cannula 800 is clamped by clamping arm 850 and mounted, as shown in FIG. 23, which depicts cannula 800 in a clamped and mounted position due to engagement between cam follower surface 854 of clamping arm 850 and a clamping arm engaging surface 874 of moveable block 870. According to an exemplary embodiment, engagement between cam follower surface 854 and a clamping arm engaging surface 874 may cause clamping arms 850 to close to a greater extent to clamp cannula 800 than the biasing force provided by spring 860. Thus, the movement of moveable block 870 may actuate clamping arm 850 to clamp cannula 800 as moveable block 870 engages clamping arm 850. Because moveable block 870 actuates clamping arms 850 by engagement between clamping arm engaging surface 874 and cam follower surface 854, clamping arms 850 may clamp and mount cannula 800 over a range of motion of moveable block 870 and clamping arms 850 (e.g., including a maximum travel distance of moveable block 870), which permits clamping arms 850 to accommodate cannulas 800 of various sizes. Further, because movement of moveable block 870 may occur once a sufficient magnetic attraction occurs between metal member 812 and magnet 872, the clamping of cannula 800 by clamping arms 850 may be automated because the moveable block 870 will move towards metal member 812, causing clamping arm engaging surfaces 874 and cam follower surfaces 854 to engage, which in turn actuates clamping arms 850 to clamp cannula 800.

Clamping arms 850 may have a single piece construction or may be made of a plurality of parts joined to one another. According to an exemplary embodiment, a clamping arm 850 may include a stiffening member 856 to reinforce the clamping arm 850. For example, if clamping arm 850 is made of a polymer, stiffening member 856 may be made of, for example, a metal.

Figure 24:
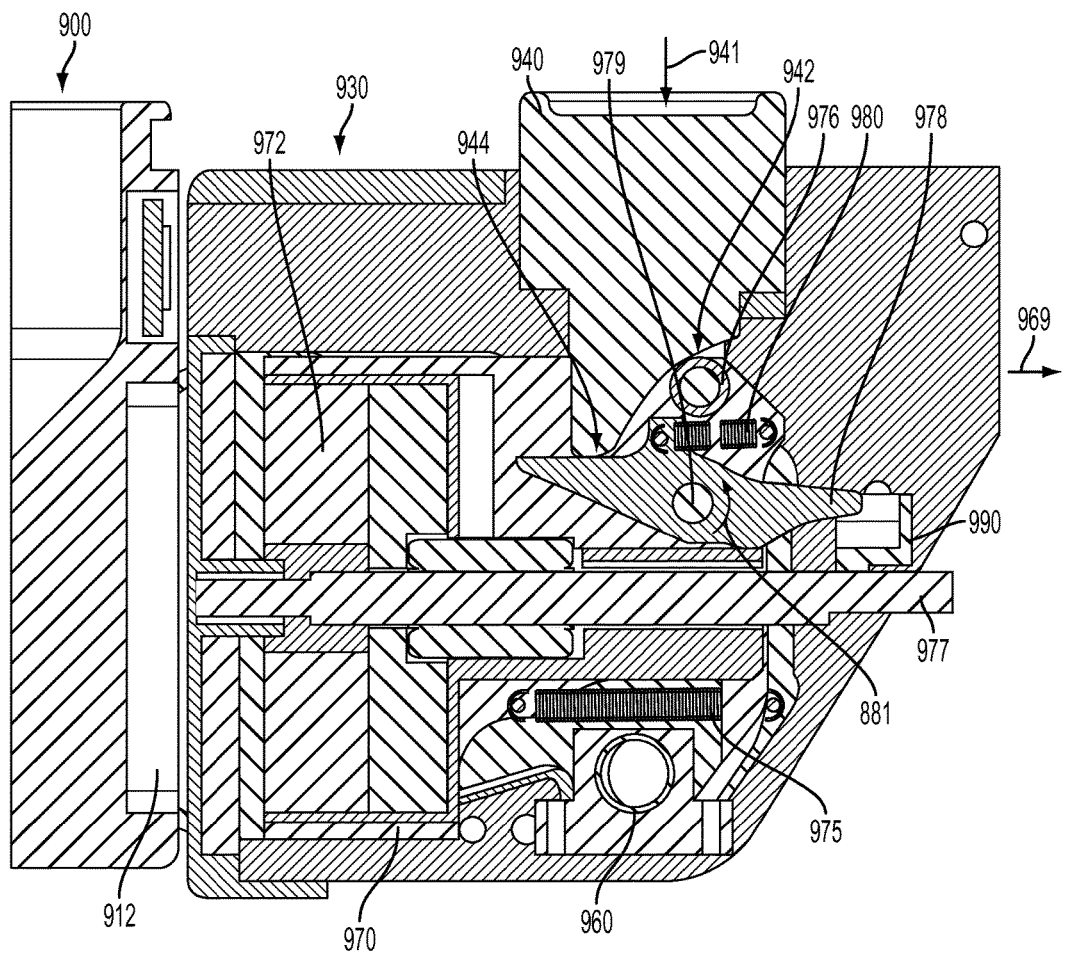
FIG. 24 is a side view, with interior portions depicted, of a cannula mounted to a cannula mount including a locking member, according to an exemplary embodiment.

According to an exemplary embodiment, a cannula mount may include a device to minimize or prevent unlocking of clamping arms from a cannula once the cannula has been mounted to the cannula mount. Turning to FIG. 24, a side cross section view is shown of a cannula 900, which includes a metal member 912, mounted to a cannula mount 930. Cannula and cannula mount 930 may be configured according to the exemplary embodiment of FIGS. 17-23. Cannula mount 930 may be, for example, cannula mount 124 provided on one of manipulator arms 110-113 of the exemplary embodiment of FIG. 1. For instance, cannula mount 930 may include a spring 960 to bias a clamping arm (not shown in FIG. 24) to a closed position, a release button 940, and a moveable block 970. Moveable block 970 may include a magnet 972 and a release engaging surface 976, may slide along a shaft 977, and may be biased to a position away from cannula 900 by a spring 975 as discussed above with regard to the exemplary embodiment of FIGS. 17-23.

Moveable block 970 may further include a locking member 978. When moveable block 970 has actuated clamping arms (not shown in FIG. 24) to clamp and mount cannula 900, locking member 978 may be positioned to engage a stop member 990 should moveable block 970 be permitted to reverse its movement along shaft 977 in direction 969 of FIG. 24, thus minimizing or preventing movement of moveable block 970 and unlocking of the clamping arms. Locking member 978 may be mounted to a pin 979 connected to moveable block 970. Locking member 978 may pivot about pin 979, although locking member 978 may be biased to the locked position shown in FIG. 24 by a biasing device, such as a spring 980 or other biasing device. Locking member 978 may be released, for example, by depressing release button 940 in direction 941. Depressing release button 940 causing a tip 944 of release button 940 to engage locking member 978, which in turn pivots about pin 979 in direction 981 against the force applied by spring 980. When locking member 978 has pivoted in direction 981, locking member 878 will no longer engage stop member 990 when moveable block 970 is moved along direction 969.

Release button 940 may also function to open clamping arms that mount a cannula. As shown in FIG. 24, release button 940 may include a curved surface 942 that engages the release engaging surface 976 (which may be, for example, a roller or a cam follower surface) of moveable block 970. Because surface 942 is curved, as release button 940 is depressed in direction 941, release engaging surface 976 follows the curvature of surface 942 and is generally moved along direction 969 with the rest of moveable block 970. As a result, moveable block 970 may move along direction 969 and become disengaged from clamping arms (e.g., clamping arm engaging surfaces 874 in FIG. 21 disengage from cam follower surfaces 854 of clamping arms 850 in FIG. 22). Release button 840 of the exemplary embodiment of FIGS. 17-23 may function in a similar manner by engaging release engaging surface 876 of moveable block 870 when release button 840 is depressed. Thus, release buttons 840, 940 may be a single mechanism that actuates clamping arms 850 to an open position and release a cannula.

Figure 25:
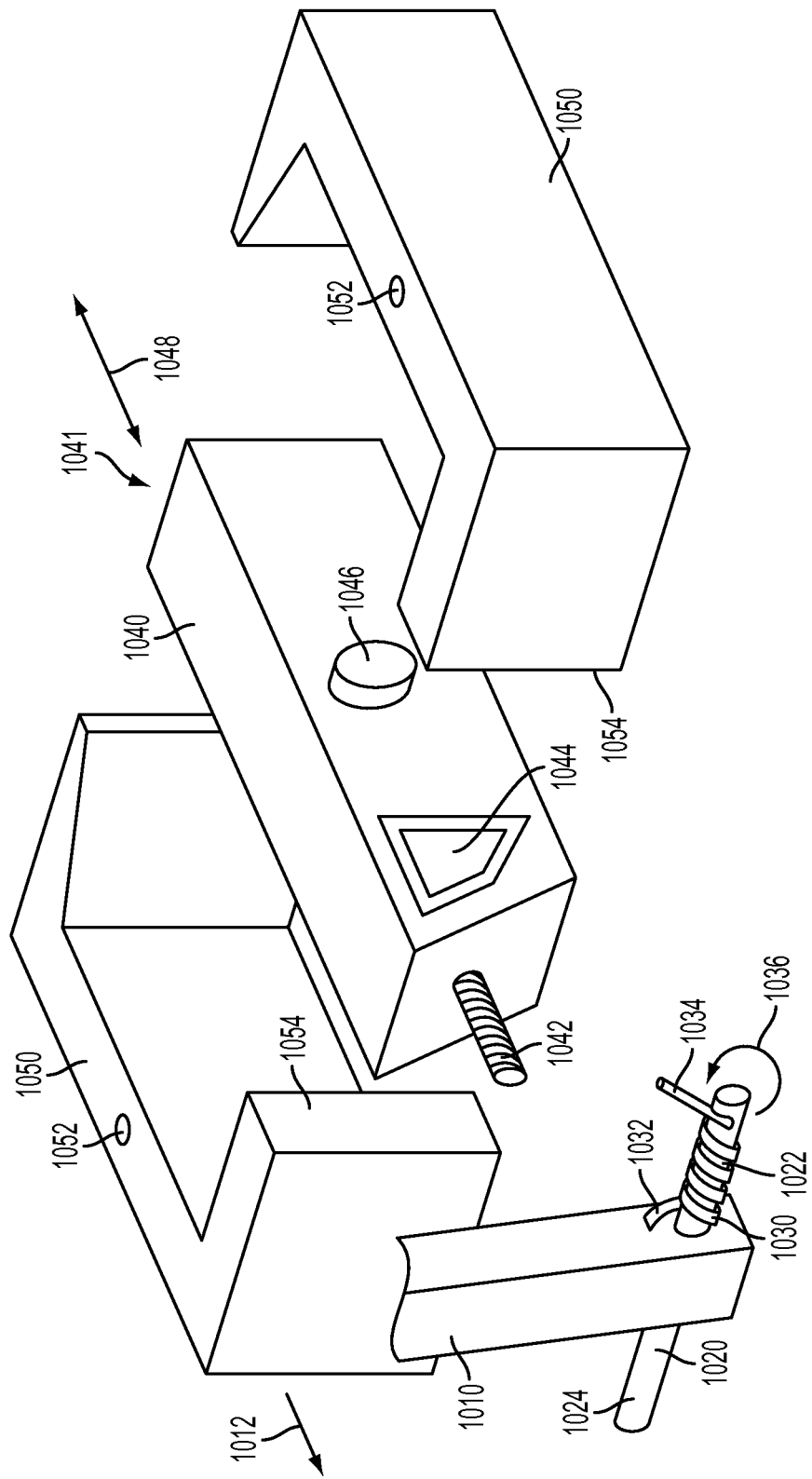
FIG. 25 is a partial exploded view of a cannula mount, according to another exemplary embodiment.

Turning to FIG. 25, another exemplary embodiment of a portion of a cannula mount is schematically shown in an exploded view. The portion of the cannula mount depicted in FIG. 25 includes clamping arms 1050 that may pivot about pins 1052. Clamping arms 1050 may each be connected to a spring (not shown) to bias clamping arms 1050 to a closed (e.g., clamping) position. The cannula mount may further include a moveable block 1040 that includes cam surfaces 1044 configured to engage cam follower surfaces 1054 of clamping arms 1050, similar to the exemplary embodiment of FIGS. 17-23. A spring 1042 may be connected to moveable block 1040 to bias moveable block 1040 along directions 1048 toward spring 1042.

According to an exemplary embodiment, moveable block 1040 may include a magnet (not shown), such as in a distal portion 1041 of moveable block 1040, similar to the exemplary embodiments of FIGS. 12-23 described above. Thus, when a cannula including a metal member (not shown) is inserted into the cannula mount, such as between clamping arms 1050, the magnet of moveable block 1040 may be attracted to the metal member of the cannula, resulting in moveable block 1040 moving along directions 1048 towards the cannula (against the force applied by spring 1042) once the cannula has been inserted a sufficient distance between clamping arms 1050. As moveable block 1040 moves forward along directions 1048, cam surfaces 1044 of moveable block 1040 may engage cam follower surfaces 1054 of clamping arms 1050, causing clamping arms 1050 to pivot, clamp upon the cannula, and mount the cannula, similar to the exemplary embodiment of FIGS. 12-23. Thus, the cannula mount partially depicted in the exemplary embodiment of FIG. 25 may clamp and mount cannulas over a range of motion of clamping arms 1050 and moveable block 1040.

The cannula mount partially depicted in the exemplary embodiment of FIG. 25 may include a mechanism to release a cannula. As shown in FIG. 25, the cannula mount may include a handle 1010 connected to a shaft 1020. A torsion spring 1030 may be wound about first end 1022 of shaft 1020, with a first end 1032 of torsion spring 1030 being connected to handle 1010 and a second end 1034 extending from shaft 1020, as shown in the exemplary embodiment of FIG. 25. Thus, when handle 1010 is actuated, such as by moving in direction 1012, shaft 1020 rotates along direction 1036, which in turn causes torsion spring 1030 and second end 1034 to rotate in direction 1036. Handle 1010, shaft 1020, and torsion spring 1030 may be positioned (such as, for example by extending handle 1010 through a hollow (not shown) in moveable block 1040) so that as second end 1034 rotates along direction 1036, second end 1034 engages a projection 1046 of moveable block 1040 and forces moveable block 1040 rearward, permitting a user to release the cannula from between clamping arms 1050.

Although a single torsion spring 1030 is shown on first end 1022 of shaft 1020 in the exemplary embodiment of FIG. 25, more than one torsion spring may be provided on shaft 1020. For example, a second torsion spring (not shown) may be provided on second end 1024 of shaft 1024 to engage a projection (similar to projection 1046) on the same side of moveable block 1040 as second end 1024. The second torsion spring may be configured similarly to torsion spring 1030 described above. Thus, when handle 1010 is actuated, each of the torsion springs would engage respective projections 1046 to force moveable block 1040 in a rearward direction to facilitate release of a cannula from the cannula mount.

By providing a cannula mount according to the various exemplary embodiments described herein, the mount may accommodate cannulas of various sizes, such as cannulas that vary in size due to a manufacturing tolerance. Further, mounting a cannula to the mount is simple and fast, yet holds cannula securely. In addition, latching of a cannula to a mount can be at least partially automated.

Further modifications and alternative embodiments will be apparent to those of ordinary skill in the art in view of the disclosure herein. For example, the devices, systems, and methods may include additional components or steps that were omitted from the diagrams and description for clarity of operation. Accordingly, this description is to be construed as illustrative only and is for the purpose of teaching those skilled in the art the general manner of carrying out the present disclosure. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the scope of the present disclosure and following claims.

It is to be understood that the particular examples and embodiments set forth herein are non-limiting, and modifications to structure, dimensions, materials, and methodologies may be made without departing from the scope of the present disclosure.

Other embodiments in accordance with the present disclosure will be apparent to those skilled in the art from consideration of the specification and practice of the invention disclosed herein. It is intended that the specification and examples be considered as exemplary only, with being entitled to their full breadth of scope, including equivalents by the following claims.

What is claimed is:

1. A cannula mount for a surgical system, the cannula mount comprising:
    a body including an aperture sized to receive a portion of a cannula;
    a pivotable clamping arm located within the aperture of the body, the clamping arm being configured to engage the portion of the cannula received in the aperture, the clamping arm comprising a cam follower surface; and
    a cam member moveable between a first position and a second position, the cam member comprising a cam surface;
    wherein on the condition that the cam member is in the first position, the cam surface engages the cam follower surface of the clamping arm to actuate the clamping arm to a closed position in which the clamping arm engages the portion of the cannula received in the aperture; and
    wherein on the condition that the cam member is in the second position, the clamping arm is free to move to an open position in which the clamping arm does not engage the cannula.

2. The cannula mount of claim 1, wherein the cannula mount comprises a pair of clamping arms actuatable by the cam member.

3. The cannula mount of claim 1, wherein, when the cam member moves from the second position to the first position, the cam surface engages and slides against the cam follower surface of the clamping arm until the portion of the cannula is clamped by the clamping arm.

4. The cannula mount of claim 1, wherein the cam member comprises a roller that engages the clamping arm.

5. The cannula mount of claim 1, further comprising one or more springs configured to bias the cam member to the first position.

6. The cannula mount of claim 5, wherein the one or more springs comprises a plurality of springs.

7. The cannula mount of claim 5, further comprising a handle configured to actuate the cam member to the second position.

8. The cannula mount of claim 7, wherein the handle is connected to the cam member by a link.

9. The cannula mount of claim 1, wherein the cam member comprises a magnet configured to interact with a metal member of the cannula when mounting the cannula to the cannula mount.

10. The cannula mount of claim 1, wherein the body is part of a manipulator arm of a patient side cart of a teleoperated surgical system.

11. The cannula mount of claim 1, further comprising a sensor configured to detect a position of the cam member.

12. A cannula mount for a surgical system, the cannula mount comprising:
a body including an aperture sized and configured to receive a portion of a cannula;
a plurality of pivotable clamping arms located within the aperture of the body, the clamping arms being configured to engage the portion of the cannula received in the aperture; and
a cam member moveable between a first position and a second position;
wherein the cam member engages each of the clamping arms in the first position to actuate the plurality of clamping arms to a closed position in which the clamping arms engage the portion of the cannula received in the aperture.

13. A teleoperated surgical system, comprising:
a cannula; and
a cannula mount comprising:
a body including an aperture sized and configured to receive a portion of the cannula;
a pivotable clamping arm located within the aperture of the body, the clamping arm being configured to apply a clamping force to the portion of the cannula received in the aperture, the clamping arm comprising a cam follower surface; and
a cam member moveable between a first position and a second position, the cam member comprising a cam surface;
wherein on the condition that the cam member is in the first position, the cam surface engages the cam follower surface of the clamping arm to actuate the clamping arm to a closed position in which the clamping arm applies the clamping force to the portion of the cannula received in the aperture;
wherein on the condition that the cam member is in the second position, the clamping arm is free to move to an open position in which the clamping arm does not apply the clamping force to the cannula.

14. The teleoperated surgical system of claim 13, wherein the body is part of a manipulator arm of a patient side cart of the teleoperated surgical system.

15. The teleoperated surgical system of claim 13, further comprising a spring configured to bias the moveable cam member to the first position.

16. The teleoperated surgical system of claim 13, further comprising a cannula sterile adaptor configured to be between the portion of the cannula and the cannula mount, wherein the clamping arm is configured to apply the clamping force through the cannula sterile adaptor to the portion of the cannula received in the aperture.

17. The teleoperated surgical system of claim 16:
wherein the cannula sterile adaptor comprises a first portion comprising a rigid material and a second portion comprising a compliant material; and
wherein the first portion comprises a depression configured to receive a respective clamping arm of a cannula mount of the surgical system.

18. The teleoperated surgical system of claim 17, wherein the second portion is made of a thermoplastic elastomer.

19. The teleoperated surgical system of claim 13, wherein the cannula comprises a metal member, and the moveable cam member comprises a magnet configured to interact with the metal member of the cannula when mounting the cannula to the cannula mount.

20. The teleoperated surgical system of claim 19, wherein a magnetic force between the magnet and the metal member pulls the cam member to the first position to actuate the pivoting clamping arm and engage the cannula when mounting the cannula to the cannula mount.

21. The teleoperated surgical system of claim 16:
wherein the cannula comprises a bowl section, a tube, and an attachment portion; and
wherein the attachment portion is the portion of the cannula configured to be received within the aperture of the body of the cannula mount when mounting the cannula to the cannula mount.

22. The teleoperated surgical system of claim 21, wherein the attachment portion comprises a depression configured to receive the clamping arm when mounting the cannula to the cannula mount.

23. The teleoperated surgical system of claim 22, wherein the depression of the attachment portion further receives the cannula sterile adaptor between the attachment portion and the clamping arm when mounting the cannula to the cannula mount.

* * * * *